United States Patent [19]

Ueda et al.

[11] Patent Number: 5,917,055
[45] Date of Patent: Jun. 29, 1999

[54] PROCESS FOR PRODUCING N-(D-α-METHYL-β-MERCAPTOPROPIONYL)-L-PROLINE AND ITS INTERMEDIATE

[75] Inventors: Yasuyoshi Ueda; Fumihiko Kanou, both of Himeji; Koichi Kinoshita, Takasago; Takahiro Okubo, Akashi, all of Japan

[73] Assignee: Kaneka Corporation, Osaka, Japan

[21] Appl. No.: 08/849,337

[22] PCT Filed: Oct. 7, 1996

[86] PCT No.: PCT/JP96/02902

§ 371 Date: Jul. 31, 1997

§ 102(e) Date: Jul. 31, 1997

[87] PCT Pub. No.: WO97/12858

PCT Pub. Date: Apr. 10, 1997

[30] Foreign Application Priority Data

Oct. 6, 1995 [JP] Japan ..................................... 7-286886
Apr. 19, 1996 [JP] Japan ..................................... 8-122727

[51] Int. Cl.$^6$ ................................................. C07D 207/16
[52] U.S. Cl. ............................................................ 548/533
[58] Field of Search ............................................. 548/533

[56] References Cited

U.S. PATENT DOCUMENTS 5,387,697  2/1995  Hen .......................................... 548/533

FOREIGN PATENT DOCUMENTS 05221966  8/1993  Japan .

Primary Examiner—Jane Fan
Attorney, Agent, or Firm—Pollock, Vande, Sande & Amernick

[57] ABSTRACT

A highly convenient and efficient process for economically producing in a high yield high-quality captopril which is remarkably reduced in the content of impurities and has a high melting point and intermediates for synthesizing the same which contain only a small amount of precursors as impurities and have excellent qualities. The process comprises subjecting an acid halide and an L-proline to the Schotten-Baumann reaction and eliminating the impurities formed as the by-products in the form of the precursors represented by general formula (5) or (6) by treating, during or after the Schotten-Baumann reaction, the aqueous medium solution with active carbon or crystallization followed by deacylation. In the formula, $R^1$ represents acyl and n represents an integer of from 2 to 4.

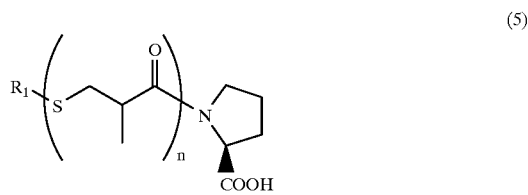

(5)

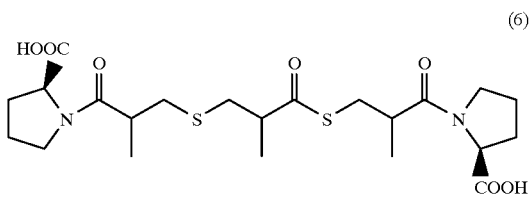

(6)

19 Claims, No Drawings

PROCESS FOR PRODUCING N-(D-α-METHYL-β-MERCAPTOPROPIONYL)-L-PROLINE AND ITS INTERMEDIATE

This is a PCT/JP96/02902 Oct. 7, 1996 now WO 97/12858 Apr. 10, 1997.

FIELD OF THE INVENTION

The present invention relates to a process for producing N-(D-α-methyl-β-mercaptopropionyl)-L-proline of the formula (4)

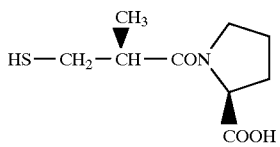

and its synthetic intermediate N-(D-α-methyl-β-acylthiopropionyl)-L-proline of the formula (3)

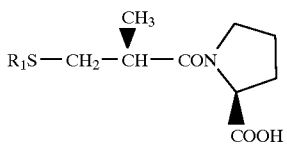

or N-(DL-α-methyl-β-acylthiopropionyl)-L-proline.

BACKGROUND TECHNOLOGY

N-(D-α-methyl-β-mercaptopropionyl)-L-proline (4) has potent angiotensin converting enzyme inhibiting activity and is an antihypertensive agent generically called captopril (erg. Biochemistry, 16, 5487 (1977)).

Various methods are known for the production of N-(D-α-methyl-β-mercaptopropionyl)-L-proline (4) (hereinafter also called captopril). For instance, in Japanese Kokoku Publication Sho-60-56705, Japanese Kokai Publication Hei-5-17435 and Japanese Kokai Publication Hei-5-221966 and elsewhere, there are disclosed processes for producing captopril which comprises deriving an N-(D-α-methyl-β-acylthiopropionyl)-L-proline (3) from a D-α-methyl-β-acylthiopropionic acid halide or DL-α-methyl-β-acylthiopropionic acid halide and L-proline by utilizing the Schotten-Baumann reaction and then subjecting the intermediate (3) to deacylation.

While the medical and medicinal expenses are on a growing trend, captopril is expectedly one of large-sale generic drugs and it is of great significance to develop a process for producing high-purity captopril at low cost and in easy and simple manner.

As for the specifications of captopril, the Japanese Pharmaceutical Index requires that the captopril bulk substance contains not less than 97.5% of captopril and has a melting point of 105° C. to 110° C. and that the content of captopril disulfide, which is one of related substances (organic impurities), is not more than 2.5%, among others. The U.S. Pharmacopeia requires, among others, that the content of β-mercapto-α-methylpropionic acid as a related substance (organic impurity) is not more than 0.1%. In view of the nature of a medicine ingredient, it is needless to say that said bulk substance can hardly contain other related substances or organic impurities not referred to in such specifications or, in other words, it is strongly desired that their contents do not exceed 0.1%.

Concerning the quality of captopril products obtained by subjecting the above-mentioned acid halide and L-proline to Schotten-Baumann reaction, followed by deacylation, the impurities possibly contained therein and the methods of preventing the formation thereof, literature references disclose, for example, as follows:

In the above-cited Japanese Kokai Publication Hei-5-221966, it is described that N-[α-methyl-β-methyl-β-hydroxycarbonyl)ethylthiopropionyl]-L-proline of the formula (7) given below, or N-acetyl-L-proline, among others, is formed as a by-product in the Schotten-Baumann reaction.

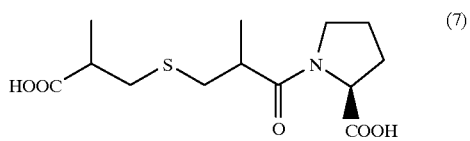

According to the teaching disclosed in said Japanese Kokai Publication Hei-5-221966, however, the Schotten-Baumann reaction and the subsequent deacylation are carried out in a continuous manner, so that it is not very certain in which step the above-mentioned by-products are formed as impurities. For preventing the formation of these products according to said teaching, the pH, temperature and D-α-methyl-β-acylthiopropionic acid halide/L-proline mole ratio, among others, are important in carrying out the Schotten-Baumann reaction. As optimal values, there are mentioned an initial pH of 9.9 to 10.1, a final pH of 10.9 to 11.0, a reaction temperature of not higher than 10° C., and a D-α-methyl-β-acylthiopropionic acid halide/L-proline mole ratio of 1.0 to 1.1.

In U.S. Pat. No. 5,387,697, it is disclosed that the compound of the formula (8)

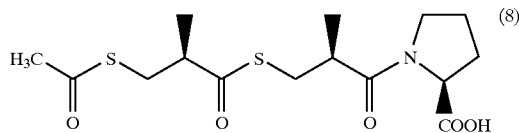

is formed as a by-product during the Schotten-Baumann reaction and it is described that for preventing the formation of this impurity, the Schotten-Baumann reaction should be carried out at 0° C. to 5° C. in 0.25 M potassium phosphate buffer solution, while adjusting the pH to 7.5 to 8.5 with potassium hydroxide. However, in said patent specification, no mention is made of N-[α-methyl-β-(β-methyl-β-hydroxycarbonyl)-ethylthiopropionyl]-L-proline (7) and no reference is made to the relation between the compound (7) and the compound of the above formula (8).

As regards the reaction conditions to be employed for preventing the formation of the compound of formula (8), which is a precursor of the compound of formula (7), in the Schotten-Baumann reaction, those described in U.S. Pat. No. 5,387,697 Specification constitute the only prior art, which, however, has the following problems: for instance, the use of the phosphate produces a problem in waste water treatment because of its eutrophication potential, the pH adjustment by adding potassium hydroxide during reaction makes the procedure complicated, and the formation of the compound of formula (8) can be prevented only to an unsatisfactory extent.

Japanese Kokai Publication Hei-7-10835 discloses a process for purifying captopril which comprises treating an acyl-protected captopril intermediate of the formula (3) given above with active carbon and radiolite in an organic solvent to thereby eliminate the disulfide represented by the formula (9) given below, which otherwise possibly gets into the product captopril.

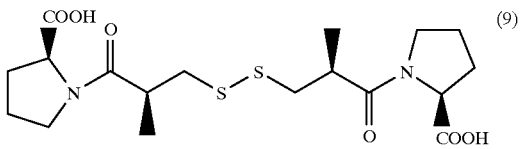

(9)

However, there is no mention whatever of the efficiency of the elimination of by-products of the formula (5) shown below and the by-product of the formula (6) shown below. In the formulas, n represents an integer of 2 to 4 and $R_1$ represents an acyl group.

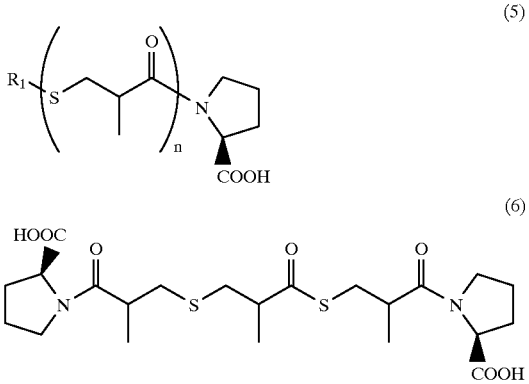

(5)

(6)

Check experiments performed by the present inventors showed that the above-mentioned treatment with active carbon etc. in organic solvents can hardly be expected to be effective in eliminating the by-products represented by the above general formula (5) or formula (6).

U.S. Pat. No. 5,387,697, CN Patent Publication 1,051,909 and CN Patent Publication 1,034,920, for instance, respectively describe the crystallization of the acyl-protected captopril intermediate of the above formula (3) from an aqueous solution thereof. In each case, the crystallization is effected at room temperature or a temperature therebelow and there is no mention whatever of the efficiency of the elimination of the by-products represented by the above general formula (5) or formula (6). Check experiments made by the present inventors, however, revealed that these methods can hardly be expected to be effective in removing the by-products represented by the above general formula (5) and the by-product represented by formula (6).

Thus, so far, neither a process for producing captopril or its acylated intermediate by which the by-product formation can be prevented nor a method of purification by which by-products can be removed from captopril or its acyl-protected intermediate contaminated therewith has been available.

As detailedly described hereinabove, the prior art captopril products obtained by the Schotten-Baumann reaction between the above-mentioned acid halide and L-proline and the subsequent deacylation are contaminated with various impurities and it is very difficult to obtain high-quality captopril.

SUMMARY OF THE INVENTION

In view of the foregoing, it is an object of the present invention to provide a very easy and simple and efficient process for economically producing in high yields high-quality N-(D-α-methyl-β-mercaptopropionyl)-L-proline (4) (captopril) containing very small amounts of various impurities, in particular N-[α-methyl-β-(β-methyl-β-hydroxycarbonyl)ethylthiopropionyl]-L-proline (7), which is difficult to eliminate, and having a high melting point.

Another object of the present invention is to provide a very easy and simple and efficient process for producing, in high yields and at low cost, an N-(D-α-methyl-β-acylthiopropionyl)-L-proline (3) or N-(DL-α-methyl-β-acylthiopropionyl)-L-proline of good quality, which serves as an intermediate in the synthesis of N-(D-α-methyl-β-mercaptopropionyl)-L-proline (4) (captopril) and contains only small amounts of the compounds of the general formula (5) shown above and the compound of formula (6), which are precursors of N-[α-methyl-β-(β-methyl-β-hydroxycarbonyl)-ethylthiopropionyl]-L-proline (7).

As a result of intensive investigations made by the present inventors concerning the each reaction method of carrying out the above-mentioned Schotten-Baumann reaction and deacylation reaction, and the purifying method in an attempt to solve the above problems, the present inventors arrived at a conclusion that for obtaining high-quality N-(D-α-methyl-β-mercaptopropionyl)-L-proline (4) (captopril) in high yield, it is very important to prevent the formation of or remove, in particular, the compounds of the above general formula (5) and the compound of the above formula (6), which are precursors of N-[α-methyl-β-(β-methyl-β-hydroxycarbonyl)-ethylthiopropionyl]-L-proline (7), and prevent, in the deacylation reaction step, the formation of N-[α-methyl-β-(β-methyl-β-hydroxycarbonyl)ethylthiopropionyl]-L-proline (7) as a by-product.

The present inventors further found that N-[α-methyl-β-(β-methyl-β-hydroxycarbonyl)ethylthiopropionyl]-L-proline (7) is formed under strongly alkaline conditions in the series of the steps for captopril formation, especially in the Schotten-Baumann reaction but, under comparatively mild alkaline conditions, it remains in the stage of a precursor or precursors as represented by the above general formula (5) or formula (6).

Based on the above findings, the present inventors concluded that it is possible to reduce the content of the compound of the above formula (7) as an impurity in captopril products when, in the process comprising the Schotten-Baumann reaction and the deacylation reaction, the following treatments are carried out, either alone or in combination, under respective specific conditions:

① treatment for reducing the formation of compounds of the above general formula (5) and the compound of formula (6), ② treatment for preventing the conversion of these compounds to the compound of the above formula (7), and ③ treatment for removing the compounds of the above general formula (5) and the compound of formula (6) by purification treatment with active carbon, crystallization or the like. In the end, they have been led to completion of the present invention.

Thus, the gist of the present invention consists in that, in the process for producing N-(D-α-methyl-β-mercaptopropionyl)-L-proline of the formula (4)

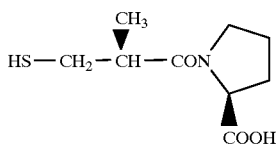

(4)

by subjecting a D-α-methyl-β-acylthiopropionic acid halide of the general formula (1)

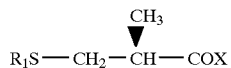

(1)

(wherein $R_1$ represents an acyl group and X represents a halogen) and L-proline of the formula (2)

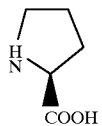

(2)

to Schotten-Baumann reaction in a basic aqueous medium in the presence of a deacidifying condensing agent to give the corresponding N-(D-α-methyl-β-acylthiopropionyl)-L-proline of the general formula (3)

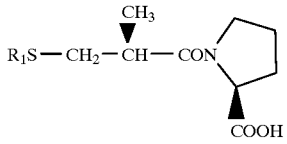

(3)

(wherein $R_1$ is as defined above), followed by deacylation, the deacylation of the N-(D-α-methyl-β-acylthiopropionyl)-L-proline is carried out after removal of those impurities concurrently formed with the above-mentioned objective substance N-(D-α-Methyl-β-mercaptopropionyl)-L-proline, in their precursor stage, from the aqueous medium solution after commencement but before completion of said Schotten-Baumann reaction or after completion thereof by treating said aqueous medium solution with active carbon at a pH not higher than 12, to give high purity N-(D-α-methyl-β-mercaptopropionyl)-L-proline (4).

In another aspect, the gist of the present invention consists in that, in the production process mentioned above, the N-(D-α-methyl-β-acylthiopropionyl)-L-proline (3) formed is collected by causing the same to perform crystallization at 35° C. to 100° C. under acidic conditions from the aqueous medium solution after completion of the Schotten-Baumann reaction, thus removing those impurities concurrently formed with the above-mentioned objective substance N-(D-α-methyl-β-mercaptopropionyl)-L-proline, in their precursor stage, and the thus-collected N-(D-α-methyl-β-acylthiopropionyl)-L-proline (3), either as such or after storage, is subjected to deacylation to thereby obtain high purity N-(D-α-methyl-β-mercaptopropionyl)-L-proline (4).

In a further aspect, the gist of the present invention consists in that, in the production process mentioned above, potassium hydrogencarbonate is caused to coexist as the deacidifying condensing agent in the step of subjecting the D-α-methyl-β-acylthiopropionic acid halide (1) and L-proline (2) to Schotten-Baumann reaction to thereby prevent the formation of the impurities which are otherwise formed in addition to the above-mentioned objective substance N-(D-α-methyl-β-mercaptopropionyl)-L-proline, in the stage of precursors thereof, to prepare the corresponding N-(D-α-methyl-β-acylthiopropionyl)-L-proline (3) with a decreased content of the precursors, which is then subjected to deacylation to give high purity N-(D-α-methyl-β-mercaptopropionyl)-L-proline (4).

DETAILED DESCRIPTION OF THE INVENTION

In the following, the present invention is described in detail.

According to the present invention, a D-α-methyl-β-acylthiopropionic acid halide (1) and L-proline (2) are subjected to Schotten-Baumann reaction. In the practice of the present invention, it is also possible to use the above-mentioned D-α-methyl-β-acylthiopropionic acid halide (1) in the form of DL-α-methyl-β-acylthiopropionic acid halide and subject the same to Schotten-Baumann reaction to give the N-(D-α-methyl-β-acylthiopropionyl)-L-proline (3) in the form of N-(DL-α-methyl-β-acylthiopropionyl)-L-proline. In the Schotten-Baumann reaction mentioned above, various side reactions are presumable as follows.

First, when exposed to water, the above-mentioned D-α-methyl-β-acylthiopropionic acid halide (1) is hydrolized to give the corresponding carboxylic acid. When this by-product carboxylic acid is formed in large quantities, the above-mentioned D-α-methyl-β-acylthiopropionic acid halide (1) becomes short and L-proline (2) partially remains unreacted. When the amount of residual L-proline (2) increases, the L-proline (2) reacts with the above-mentioned acid halide (1), the N-(D-α-methyl-β-acylthiopropionyl)-L-proline (3) or N-(DL-α-methyl-β-acylthiopropionyl)-L-proline to give, as by-products, the corresponding N-acyl-L-proline, N-(D-α-methyl-β-mercaptopropionyl)-L-proline (4) or N-(DL-α-methyl-β-mercaptopropionyl)-L-proline, etc.

In this way, side reactions based on the acyl group elimination or migration are apt to occur in the reaction system and, furthermore, compounds of the above general formula (5) or the compound represented by formula (6) are readily formed as by-products in said system. The by-products represented by the above general formula (5) or formula (6) are converted, under alkaline deacylation reaction conditions, to N-[α-methyl-β-(β-Methyl-β-hydroxycarbonyl)ethylthiopropionyl]-L-proline, which is very difficult to remove.

It has not yet been reported that the above-mentioned compounds (5) and compound (6) are precursors of the compound of the above formula (7) but is a novel finding obtained by the present inventors.

Among the compounds represented by the above general formula (5) which are formed as products in the Schotten-Baumann reaction employed in the process of the present invention, the proportion of that compound of n=2 is high and the formation of this by-product has a great influence on the formation, as a by-product, of N-[α-methyl-β-(β-methyl-β-hydroxycarbonyl)ethylthiopropionyl]-L-proline (7).

In accordance with the present invention, for obtaining captopril with a very low content of impurities such as N-[α-methyl-β-(β-methyl-β-hydroxycabonyl)ethylthiopropionyl]-L-proline (7), the aqueous medium solution after commencement but before completion of the Schotten-Baumann reaction or after completion of said reaction is treated with active carbon, or the N-(D-α-methyl-β-acylthiopropionyl)-L-proline (3) in the form of crystals or an oily substance, for instance, is treated with active carbon in an aqueous medium, to thereby remove the impurities formed as by-products concurrently with the above-mentioned objective substance N-(D-α-methyl-β-mercaptopropionyl)-L-proline (4) in their precursor stage and, thereafter, the deacylation is carried out.

As the above-mentioned impurities, which are formed as by-products together with the objective substance, there may be mentioned, for instance, the above-mentioned N-[α-methyl-β-(β-methyl-β-hydroxycarbonyl) ethylthiopropionyl]-L-proline (7) etc. As the above-mentioned precursors, there may be mentioned the above-mentioned compounds represented by the general formula (5) and the compound of formula (6).

The conditions for the above-mentioned active-carbon treatment are preferably such that the precursors mentioned above are not converted to N-[α-methyl-β-(β-methyl-β-hydroxycarbonyl)ethylthiopropionyl]-L-proline (7) etc., and the N-(D-α-methyl-β-acylthiopropionyl)-L-proline (3) or N-(DL-α-methyl-β-acylthiopropionyl)-L-proline does not undergo deacylation to give N-(D-α-methyl-β-mercaptopropionyl)-L-proline (4) or N-(DL-α-methyl-β-mercapto-propionyl)-L-proline or is not converted to the disulfide. From this viewpoint, the pH to be employed in the above treatment step is generally not higher than 12 although it depends on the treatment temperature and treatment period. At a pH exceeding 12, the above-mentioned conversion of the precursors may unfavorably occur. The preferred range of pH is 1 to 11, more preferably pH 2 to 10, and most preferably pH 3 to 9. Within the above-mentioned range, a pH around neutrality is suitably selected, since the N-(D-α-methyl-β-acylthiopropionyl)-L-proline (3) and N-(DL-α-methyl-β-acylthiopropionyl)-L-proline, for instance, show low solubility under acidic conditions.

In the above-mentioned active-carbon treatment, the concentration of the N-(D-α-methyl-β-acylthiopropionyl)-L-proline (3) or N-(DL-α-methyl-β-acylthiopropionyl)-L-proline is not limited to any particular level but is preferably one at which the N-(D-α-methyl-β-acylthiopropionyl)-L-proline (3) or N-(DL-α-methyl-β-acylthiopropionyl)-L-proline is completely dissolved. Said concentration can be selected taking into consideration of the above as well as the operability of each individual treatment procedure employed and so forth.

The acid to be used for pH adjustment in the above active-carbon treatment is not limited to any particular species but includes, among others, mineral acids such as hydrochloric acid and sulfuric acid. The base to be used for pH adjustment is not limited to any particular species, either. Thus, said base may be such an inorganic base as sodium hydroxide, potassium hydroxide, lithium hydroxide, sodium carbonate, potassium carbonate, lithium carbonate, sodium hydrogencarbonate, potassium hydrogencarbonate or lithium hydrogencarbonate, or, where appropriate, it may be an organic base such as an amine, which can form a salt with the carboxyl group of the N-(D-α-methyl-β-acylthiopropionyl)-L-proline (3) or N-(DL-α-methyl-β-acylthiopropionyl)-L-proline to thereby increase the solubility thereof. These acids or bases may be used either singly or in combination as a mixture of two or more. Among them, preferred acids are hydrochloric acid and sulfuric acid, and preferred bases are sodium hydroxide, potassium hydroxide and lithium hydroxide.

In the above-mentioned active-carbon treatment, the treatment temperature can be adequately selected within the range from freezing temperature to boiling point depending on the pH, treatment time and other factors. Generally, a temperature around room temperature or below is preferred.

In the above-mentioned active-carbon treatment, the amount of active carbon to be used can be adequately selected taking into consideration of the active carbon species employed, the elimination effect thereof, the contents of the above-mentioned precursor substances, and so on.

In the above-mentioned active-carbon treatment, the time required therefor can be known by high-performance liquid chromatography monitoring, When powder-form active carbon is used, it is generally about 1 hour. In this case, granular active carbon can be used and it is convenient to employ a method comprising passing the above-mentioned aqueous medium solution containing the N-(D-α-methyl-β-acylthiopropionyl)-L-proline (3) through a column packed with granular active carbon, for instance.

In the practice of the present invention, it is also possible, in the above-mentioned active-carbon treatment, to use an active carbon species having low oxidizing activity or combinedly use a reducing agent so that the conversion of N-(D-α-methyl-β-mercaptopropionyl)-L-proline (3) or N-(DL-α-methyl-β-mercaptopropionyl)-L-proline, which results from deacylation, to the corresponding disulfide can be prevented.

In the practice of the present invention, the above-mentioned active-carbon treatment is applied to the aqueous medium solution after commencement but before completion of the Schotten-Baumann reaction or after completion of said reaction. As said aqueous medium solution, the Schotten-Baumann reaction mixture can be generally used as such. Thus, for instance, the reaction mixture obtained after carrying out the Schotten-Baumann reaction at a pH of about 7 to 12 or the reaction mixture obtained after carrying out the Schotten-Baumann reaction in accordance with the present invention can suitably be used as such.

In that case, the above-mentioned Schotten-Baumann reaction and the active-carbon treatment can also be performed simultaneously. In this case, it is sufficient that an adequate amount of active carbon be caused to coexist, at a time optionally selected, in the reaction system for carrying out the so-far known Schotten-Baumann reaction between the D-α-methyl-β-acylthiopropionic acid halide (1) or DL-α-methyl-β-acylthiopropionic acid halide and L-proline in an aqueous medium. However, it is preferable, from the viewpoint of suppressing the adsorption loss of the D-α-methyl-β-acylthiopropionic acid halide (1) or DL-α-methyl-β-acylthiopropionic acid halide, to add during the latter half of the reaction period.

The above-mentioned aqueous medium solution to be subjected to active-carbon treatment is generally the reaction mixture obtained by carrying out the Schotten-Baumann reaction under conditions selected from among the following: the mole ratio of the above-mentioned acid halide (1) to L-proline (2)=about 0.5 to 1.2; pH 7 to 12; and reaction temperature not higher than 10° C. However, the reaction conditions are not limited to those mentioned above.

The above-mentioned active-carbon treatment is preferably carried out in an inert atmosphere, such as a nitrogen atmosphere, so that the formation of oxidized by-product can be restricted to a minimum.

The above-mentioned active-carbon treatment according to the present invention, if conducted using active carbon in combination with an organic solvent, will be ineffective but, when carried out using active carbon in combination with an aqueous medium, in particular water, produces an unexpectedly marked effect. Thus, said treatment is very advantageous in that it can be carried out in water without using any organic solvent.

The above-mentioned active-carbon treatment can also be used in a method of purifying the N-(D-α-methyl-β-acylthiopropionyl)-L-proline (3) or N-(DL-α-methyl-β-acylthiopropionyl)-L-proline, which contains such impurity precursors as represented by the above general formula (5) or formula (6), to give a high purity product. In this case, the medium can be an aqueous one as in the case of the above-mentioned Schotten-Baumann reaction mixture.

The above-mentioned active-carbon treatment in accordance with the present invention results not only in removal of the precursors of N-[α-methyl-β-(β-methyl-β-hydroxycarbonyl)-ethylthiopropionyl]-L-proline (7) but also in removal of the unreacted D-α-methyl-β-acylthiopropionic acid halide (1), which has an inhibitory effect on the crystallization of captopril in aqueous medium, and the by-product D-α-methyl-β-acylthiopropionic acid formed by hydrolysis, so that the crystallization of captopril in aqueous medium becomes very easy and high quality captopril can be obtained. Thus, a continuous process in aqueous medium comprising, for example, Schotten-Baumann reaction→active-carbon treatment→deacylation reaction→captopril crystallization, which process does not require isolation of the N-(D-α-methyl-β-acylthiopropionyl)-L-proline (3), or, in other words, a production process by which very high quality captopril can be isolated and obtained in an easy and simple and efficient manner can be realized.

It is of course possible as well to extract the N-(D-α-methyl-β-acylthiopropionyl)-L-proline (3) or N-(DL-α-methyl-β-acylthiopropionyl)-L-proline from the solution after the above-mentioned active-carbon treatment using an organic solvent such as ethyl acetate or methylene chloride.

In another embodiment of the present invention, for obtaining captopril with a very low content of impurities such as N-[α-methyl-β-(β-methyl-β-hydroxycarbonyl)-ethylthiopropionyl]-L-proline (7), the compounds of the above general formula (5) and the compound of the above formula (6), which are precursors of the compound of the above formula (7), can be removed by causing the above-mentioned N-(D-α-methyl-β-acylthiopropionyl)-L-proline (3) or N-(DL-α-methyl-β-acylthiopropionyl)-L-proline to crystallize out from the aqueous medium solution after completion of the above-mentioned Schotten-Baumann reaction at 35° C. to 100° C. under acidic conditions.

The aqueous medium solution to be used in the above crystallization is not limited to any particular species but may be, for example, the reaction solution or post-treatment solution obtained after the Schotten-Baumann reaction carried out by the prior art methods or after the Schotten-Baumann reaction or active-carbon treatment in accordance with the present invention, or an aqueous medium solution of the N-(D-α-methyl-β-acylthiopropionyl)-L-proline (3) or N-(DL-α-methyl-β-acylthiopropionyl)-L-proline once isolated in the form of an oil or crystals. In cases other than the crystallization from the reaction mixture, the same medium as mentioned hereinabove as the aqueous medium for carrying out the Schotten-Baumann reaction can be used.

The above-mentioned crystallization can be effected by first warming and then adjusting to the conditions mentioned above by acidification and cooling. The pH in the step of warming is preferably not higher than 11, more preferably within the range of 1 to 10, most preferably within the range of 2 to 9. The warmed aqueous medium solution is then acidified and/or cooled as necessary so that the N-(D-α-methyl-β-acylthiopropionyl)-L-proline (3) or N-(DL-α-methyl-β-acylthiopropionyl)-L-proline can crystallize out at a temperature of 35° C. to 100° C. and a pH of 4.5 or below. When the pH is higher than 4.5, the deposition of crystals is insufficient and the yield becomes low.

Thus, for instance, when a solution with a pH not lower than about 5 or the Schotten-Baumann reaction mixture approximately at neutral is subjected to the crystallization step, the crystallization is effected at a final pH of about 4.5 or below, generally at a pH of 3.5 or below, preferably at a pH of about 1 to 3. A pH of 2 or below is preferred to maximize the yield of crystals. The rate of the above-mentioned acidification is not limited to any particular level but, for producing the effects of the present invention to the full, the rate of change in pH from the time of start of crystallization (the crystallization generally starts at pH of 3.5 to 4.5) should preferably be about 0.4 pH unit or lower, more preferably about 0.2 pH unit or lower, per about 15 minutes so that the above-mentioned precursors can be removed efficiently and good crystal growth can be secured. The pH at which the above-mentioned crystallization starts may vary depending on the yield of the Schotten-Baumann reaction, however.

The above-mentioned crystallization is effected at a temperature not lower than about 35° C., preferably not lower than about 40° C., more preferably not lower than about 45° C. in particular at a temperature not lower than about 50° C. Excessively high temperatures, however, cause separation of the N-(D-α-methyl-β-acylthiopropionyl)-L-proline (3) or N-(DL-α-methyl-β-acylthiopropionyl)-L-proline as an oil. Considering this, an upper limit can readily be prescribed. Thus, it is recommendable that the crystallization be effected at a temperature not higher than about 100° C., preferably not higher than about 90° C., more preferably not higher than about 70° C. When the temperature is too low, the elimination of the above-mentioned precursors may become very poorly effective and/or the characteristics of crystals may become deteriorated. Hence, the above range is recommended. In the case of N-(D-α-methyl-β-acetylthiopropionyl)-L-proline (3), the crystallization is suitably carried out generally at about 35° C. to 70° C. preferably at about 40° C. to 70° C., more preferably at about 45° C. to 65° C., in particular at about 50° C. to 60° C.

The acid or base to be used for pH adjustment in the above crystallization is not limited to any particular species but includes such mineral acids as hydrochloric acid and sulfuric acid, and such inorganic bases as sodium hydroxide, potassium hydroxide, lithium hydroxide, sodium carbonate, potassium carbonate, lithium carbonate, sodium hydrogencarbonate, potassium hydrogencarbonate and lithium hydrogencarbonate. Furthermore, where appropriate, bases capable of forming salts with the carboxyl group of the N-(α-methyl-β-acylthiopropionyl)-L-proline (3) and thereby increasing the solubility thereof, including organic bases such as amines may also be used. These acids and bases may be used singly or two or more of them may be used in combination. Among them, preferred acids are hydrochloric acid and sulfuric acid, and preferred bases are sodium hydroxide, potassium hydroxide and lithium hydroxide.

In the above-mentioned crystallization, an alternative operation of crystallization may also be employed which comprises cooling an acidic aqueous solution containing the N-(D-α-methyl-β-acylthiopropionyl)-L-proline (3) or N-(DL-α-methyl-β-acylthiopropionyl)-L-proline in an oily state.

In the above case, an aqueous medium solution containing the N-(D-α-methyl-β-acylthiopropionyl)-L-proline (3) or N-(DL-α-methyl-β-acylthiopropionyl)-L-proline, such as the Schotten-Baumann reaction mixture, is heated, for example, to a temperature not lower than about 60° C. to 70° C. and an acid or acid solution is added at an arbitrary rate to the solution to reduce the pH to 4 to 5 or below, preferably about 3.5 or below so that the separation is caused as an oil, or an aqueous medium slurry containing the N-(D-α-methyl-β-acylthiopropionyl)-L-proline (3) or N-(DL-α-methyl-β-acylthiopropionyl)-L-proline with a pH of 4 to 5 or below, preferably about 3.5 or below is heated to a temperature not lower than about 60° C. to 70° C. to cause conversion to an oily state. The oily above-mentioned solution is then cooled, whereupon the N-(D-α-methyl-β-acylthiopropionyl)-L-proline (3) or N-(DL-α-methyl-β-acylthiopropionyl)-L-proline crystallizes.

The rate of cooling in the above procedure is not particularly limited but, for producing the effects of the present invention to the full, the cooling in the crystallization step is preferably conducted at a rate of change of about 1° C. or less, preferably about 0.5° C. or less, per about 15 minutes so that the above-mentioned precursor can be removed efficiently and good crystal growth can be secured. In the case of N-(D-α-methyl-β-acetylthiopropionyl)-L-proline (3), the crystallization is generally caused by cooling to about 65° C. or below.

The above-mentioned method of crystallization generally gives a yield of about 80% to 90% or higher. For finally increasing the yield to about 90% to 95% or even higher, the solution can be cooled to about 30° C. or below. For decreasing the solubility of the N-(D-α-methyl-β-acylthiopropionyl)-L-proline (3), the crystallization procedure may include causing an inorganic salt such as sodium chloride to coexist in the solution.

As is detailedly mentioned later herein, when the crystallization is effected at low temperatures, not only the impurities such as the above-mentioned precursor substance of N-[α-methyl-β-(β-methyl-β-hydroxycarbonyl) ethylthiopropionyl]-L-proline (7), are difficult to eliminate but also minute crystals deposit or precipitate to convert the system into a whippy slurry, which worsens the fluidity or filtrability. The thus-obtained crystals have a high liquid content, are difficult to handle and are rather resistant to drying. These are serious problems in commercial production of captopril. On the contrary, the method of crystallization according to the present invention gives crystals which are not only highly pure but also are satisfactorily rod-like, hence produces additional effects in that the fluidity and filtrability of the slurry are very good and the liquid content is also low. Thus, the present invention can provide a excellent method of crystallization from the industrial production viewpoint. The case in which the whippy slurry obtained is subjected to heating treatment in the above manner also falls within the scope of the present invention. Needless to say, in this case, too, not only the quality but also the fluidity and filtrability of the slurry, and the liquid content of crystals, among others, can be improved.

In the crystallization method according to the present invention, the concentration of the N-(D-α-methyl-β-acylthiopropionyl)-L-proline (3) or N-(DL-α-methyl-β-acylthiopropionyl)-L-proline relative to the aqueous medium is not particularly limited. From the viewpoints of productivity, yield and slurry fluidity, among others, however, a concentration of about 15% to about 30% (w/v) is generally employed. When the crystallization is effected at room temperature on said concentration, a whippy slurry substantially lacking fluidity results and seriously reduces the operability on a commercial scale.

For preventing the formation of oxidated by-products, the crystallization step according to the invention is preferably carried out in an inert atmosphere, for example a nitrogen atmosphere.

Furthermore, when that reaction mixture or post-treatment mixture containing the N-(D-α-methyl-β-acylthiopropionyl)-L-proline (3) with a low content of the above-mentioned precursor substances and other impurities as obtained by carrying out the reaction method or treatment method under those Schotten-Baumann reaction conditions or active-carbon treatment conditions detailedly described later herein, or those crystals are used, the N-(D-α-methyl-β-acylthiopropionyl)-L-proline (3) with an even higher quality can be obtained. Furthermore, when an active-carbon-treated solution, from which not only the precursors of N-[α-methyl-β-(β-methyl-β-hydroxycarbonyl)-ethylthiopropionyl]-L-proline (7) but also the unreacted D-α-methyl-β-acylthiopropionic acid halide (1) or DL-α-methyl-β-acylthiopropionic acid halide and the hydrolysis by-product D-α-methyl-β-acylthiopropionic acid or DL-α-methyl-β-acylthiopropionic acid, among others, have been removed, is used, the N-(D-α-methyl-β-acylthiopropionyl)-L-proline (3) or N-(DL-α-methyl-β-acylthiopropionyl)-L-proline can be obtained with a very high quality.

The crystallization method mentioned above can be efficiently used in a method of purifying the N-(D-α-methyl-β-acylthiopropionyl)-L-proline (3) or N-(DL-α-methyl-β-acylthiopropionyl)-L-proline contaminated with such impurity precursor substances as the compounds of general formula (5) or formula (6) to give a high purity product. As the medium in this case, an aqueous medium can be used as well as the above-mentioned Schotten-Baumann reaction mixture.

Since the crystallization method according to the present invention has an operability-improving effect as mentioned above, it is needless to say that said method can also be effectively applied, for instance, to the N-(D-α-methyl-β-acylthiopropionyl)-L-proline (3) or N-(DL-α-methyl-β-acylthiopropionyl)-L-proline free of the above-mentioned precursor substances etc.

In another embodiment of the present invention, for obtaining captopril with a very low content of the impurity represented by N-[α-methyl-β-(β-methyl-β-hydroxycarbonyl)-ethylthiopropionyl]-L-proline (7), potassium hydrogencarbonate is used as the deacidifying condensing agent in the above Schotten-Baumann reaction. This is based on the finding obtained by the present inventors that the use of potassium hydrogencarbonate can lead to marked suppression of the formation of the above-mentioned compounds of general formula (5) and formula (6), which are precursors of the above-mentioned compound of formula (7). As compared with other alkali metal carbonates such as sodium carbonate, potassium carbonate, lithium carbonate and sodium hydrogencarbonate and other inorganic bases and organic bases, potassium hydrogen-carbonate was found to be an excellent deacidifying condensing agent not only specifically effective in preventing the formation of the compounds mentioned above but capable of being charged to a high concentration and leading to the formation of the N-(D-α-methyl-β-acylthiopropionyl)-L-proline in high yields.

In addition, the use of potassium hydrogencarbonate as the deacidifying condensing agent in the Schotten-Baumann reaction makes it possible to maintain the pH during reaction within the range of 7.3 to 10.2, preferably 7.5 to 9.0, which is desirable for preventing the formation of the above-mentioned precursors of compound (7), namely the compounds of general formula (5) and formula (6), without requiring pH control with a strong alkali such as sodium hydroxide or potassium hydroxide before starting the reaction and in the course thereof. Since, thus, no special pH control procedure is essentially required during the reaction, a very easy and simple process for synthesizing high purity captopril can be provided.

In carrying out the Schotten-Baumann reaction using potassium hydrogencarbonate as the deacidifying condensing agent according to the present invention, the mole ratio between the D-α-methyl-β-acylthiopropionic acid halide (1) or DL-α-methyl-β-acylthiopropionic acid halide and potassium hydrogencarbonate is desirably not less than 1.6, preferably not less than 2.0, and the mole ratio between said acid halide and L-proline is desirably 0.7 to 1.1, preferably 1. Generally, the reaction is carried out at a temperature of about 10° C. or below but not causing freezing of the solution. No particular limitations are imposed on the charged concentrations but, generally, L-proline is used in a proportion of about 10 to 100% (w/v) relative to the solvent.

The reaction solvent may be water alone or a combination of water and an organic solvent. In the latter case, from the organic solvent recovery and other viewpoints, an organic solvent immiscible with water may be used to provide a heterogeneous two-layer system.

The reaction is caused to proceed by adding the D-α-methyl-β-acylthiopropionic acid halide (1) or DL-α-methyl-β-acylthiopropionic acid halide (hereinafter, the D-α-methyl-β-acylthiopropionic acid halide (1) or DL-α-methyl-β-acylthiopropionic acid halide is sometimes referred to merely as "acid halide") to an aqueous medium containing L-proline (2). The deacidifying condensing agent potassium hydrogencarbonate may be added either in advance to the aqueous medium prior to the addition of acid halide, or successively or portionwise simultaneously with the addition of acid halide. Preferably, the unreacted acid halide is not allowed to remain in the system for a long period.

The deacidifying condensing agent potassium hydrogencarbonate may be used either by itself or in combination with such an inorganic base as sodium hydroxide, potassium hydroxide, lithium hydroxide, sodium carbonate, lithium carbonate or sodium hydrogencarbonate, or such an organic base as pyridine or triethylamine, for instance.

The above-mentioned embodiments of the present invention, namely the active-carbon treatment of an aqueous medium solution of the N-(D-α-methyl-β-acylthiopropionyl)-L-proline (3) at a pH not higher than 12, the crystallization of the N-(D-α-methyl-β-acylthiopropionyl)-L-proline (3) from an aqueous medium solution thereof at 35° C. to 100° C. under acidic conditions, and the use of potassium hydrogencarbonate as the deacidifying condensing agent in the Schotten-Baumann reaction between the acid halide and L-proline, may of course be employed either individually or combinedly.

In the following, those modes for carrying out the Schotten-Baumann reaction which is suited for application of the present invention is described in detail.

The D-α-methyl-β-acylthiopropionic acid halide (1) or DL-α-methyl-β-acylthiopropionic acid halide to be used as a starting substance in the Schotten-Baumann reaction can be prepared, for example by those processes described in Japanese Kokai Publication Sho-55-38386, Sho-55-118455 and Hei-1-222798, Japanese Kokoku Publication Sho-61-30666, and Chem. Phar. Bull., 30 (9), 3139–3146 (1982). In such processes, for example, the corresponding carboxylic acid, namely D-α-methyl-β-acylthiopropionic acid or DL-α-methyl-β-acylthiopropionic acid is first prepared and it is then treated with a halogenating reagent such as thionyl chloride, oxalyl dichloride, phosphorus trichloride, phosphorus tribromide or thionyl bromide. D-α-methyl-β-acylthiopropionyl chlorides or DL-α-methyl-β-acylthiopropionyl chlorides which can readily be prepared by using thionyl chloride, among others, can be preferably used in the practice of the present invention. As the acyl group of said D-α-methyl-β-acylthiopropionic acid halide (1) or DL-α-methyl-β-acylthiopropionic acid halide, there may be mentioned acetyl, propionyl, benzoyl and the like. Among them, acetyl is preferred.

For preventing, in the Schotten-Baumann reaction, the formation of the compounds of general formula (5) and formula (6), which are precursors of the impurity of formula (7), the following conditions are desirable: pH of 7.3 to 10.2, temperature of about 10° C. or below but not causing freezing the solution, intensity of stirring of at least 0.1 kW/m$^3$, and acid halide (1)/L-proline (2) mole ratio of 0.7 to 1.1, preferably 1. In cases where the D-α-methyl-β-acylthiopropionic acid halide (1) is submitted to the reaction in the form of DL-α-methyl-β-acylthiopropionic acid halide, the DL-form is used in an amount of 0.7 to 1.1 moles per mole of L-proline (2).

The charged concentrations are not particularly limited but, generally, about 10 to 100% (w/v) relative to the solvent as expressed in terms of L-proline concentration is used.

The reaction solvent may be water, which is a basic aqueous media, by itself or a combination of water and an organic solvent. In this case, from the organic solvent recovery viewpoint, among others, an organic solvent immiscible with water may be used to thereby provide a heterogeneous two-layer system.

The reaction is effected by adding the D-α-methyl-β-acylthiopropionic acid halide (1) or DL-α-methyl-β-acylthiopropionic acid halide to a basic aqueous medium containing L-proline (2) and a deacidifying condensing agent. The deacidifying condensing agent is used in an amount matched to the amount of the acid halide added, and is added either successively or portionwise. Preferably, the unreacted acid halide is not allowed to remain in the system for a long period.

As said deacidifying condensing agent, there may be mentioned inorganic bases such as sodium hydroxide, potassium hydroxide, lithium hydroxide, sodium carbonate, potassium carbonate, lithium carbonate, sodium hydrogencarbonate and potassium hydrogencarbonate as well as organic amines such as pyridine, triethylamine and the like.

In the following, the above-mentioned pH condition and stirring intensity are detailedly explained.

In carrying out the Schotten-Baumann reaction in the practice of the present invention, pH 7.3 to 10.2 is employed as the pH when the acid halide is added to a basic aqueous solution containing L-proline (2) and a deacidifying condensing agent. The pH is preferably 7.5 to 10.0, more preferably 8.0 to 9.8. The pH may be that basicity which is obtained with the deacidifying condensing agent. Any other basic substance having buffer action may be caused to coexist. When the pH is too low, the acid halide may be hydrolyzed to give the corresponding carboxylic acid, etc. as by-products, resulting in decreased yields. If the pH is excessively high, by-products such as the N-acyl-L-proline, N-(D-α-methyl-β-mercaptopropionyl)-L-proline (4) or N-(DL-α-methyl-β-mercaptopropionyl)-L-proline and further the above-mentioned compounds of general formula (5) or formula (6), i.e. precursors of N-[α-methyl-β-(β-methyl-β-hydroxycarbonyl)ethylthiopropionyl]-L-proline (7) tend to be formed in increased amounts. For preventing the formation of these by-products and securing high quality and high yields, and particularly for restricting the formation of N-[α-methyl-β-(α-methyl-β-hydroxycarbonyl)ethylthiopropionyl]-L-proline (7), which gets into captopril and is difficult to remove, in its precursor stage to a minimum, it is necessary that the pH be maintained in the above-mentioned range.

The intensity of stirring in the step of adding the acid halide to a basic aqueous solution containing L-proline (2) and a deacidifying condensing agent and allowing the reaction to proceed, is generally not less than about 0.1 kW/m³, preferably not less than 0.2 kW/m³, more preferably not less than about 0.5 kW/m³, especially not less than about 1.0 kW/m³. While a greater stirring intensity is desirable, the capacity of the stirrer serves as a restricting factor and, generally, there is an upper limit of about 5 kW/m³. When the stirring intensity is below the above-mentioned value, various side reactions such as hydrolysis of the acid halide and formation of the above-mentioned compounds of formula (5) and formula (6), which are precursors of N-[α-methyl-β-(β-methyl-β-hydroxycarbonyl)ethylthiopropionyl]-L-proline (7) are apt to occur, hence the proportion of the desired main reaction between the acid halide and L-proline (2) decreases. By maintaining the above-mentioned stirring intensity, the formation of the above-mentioned compounds of formula (5) and formula (6), which are precursors of N-[α-methyl-β-( -methyl-β-hydroxycarbonyl)-ethylthiopropionyl]-L-proline (7), and other by-products can be suppressed.

In the following, deacylation reaction modes suited for the practice of the present invention are described in detail.

In the practice of the present invention, the N-(D-α-methyl-β-acylthiopropionyl)-L-proline (3) obtained by the above-mentioned Schotten-Baumann reaction is further deacylated. When the D-α-methyl-β-acylthiopropionic acid halide (1) is subjected to the Schotten-Baumann reaction in the form of DL-α-methyl-β-acylthiopropionic acid halide, the N-(DL-α-methyl-β-acylthiopropionyl)-L-proline obtained is subjected to optical resolution and the resulting D-form, namely N-(D-α-methyl-β-acylthiopropionyl)-L-proline (3) is further deacylated. Irrespective of the experience of optical resolution, said N-(D-α-methyl-β-acylthiopropionyl)-L-proline (3) is preferably one obtained after the active-carbon treatment according to the present invention and/or the crystallization according to the present invention. Particularly when a D-α-methyl-β-acylthiopropionic acid halide (1) is used as the acid halide, those crystals that are once collected by subjecting the reaction mixture solution from the above-mentioned Schotten-Baumann reaction as such or after active-carbon treatment in the vicinity of neutral to crystllization treatment at a temperature of 35° C. or above under acidic conditions at a pH of 4.5 or below, preferably pH of 3.5 or below can be preferably used, optionally after storage.

In the above-mentioned deacylation reaction step, since N-[α-methyl-β-(β-methyl-β-hydroxycarbonyl)ethylthiopropionyl]-L-proline (7) is formed from the above-mentioned compounds of general formula (5) and formula (6), among others, it is desirable that the reaction mode be selected so as to minimize the formation of said compound (7). Therefore, in accordance with the present invention, the above-mentioned deacylation reaction is carried out in an alkaline aqueous medium. As the aqueous medium, use can be made of the same aqueous medium as that used in the Schotten-Baumann reaction. Thus, it is possible to carry out the Schotten-Baumann reaction, active-carbon treatment and deacylation in one and the same reaction vessel.

From the viewpoint of inhibiting impurity formation, the alkali to be used in the above deacylation reaction is preferably an alkali metal hydroxide such as sodium hydroxide, potassium hydroxide or lithium hydroxide. These may be used each alone or two or more of them may be used combinedly.

As regards the amount of the above-mentioned alkali, generally, it is conveniently used, in the case of sodium hydroxide, in a concentration of about 30% by weight or higher in aqueous solution.

The pH to be employed in the above deacylation reaction is not less than 8, although it depends on the reaction temperature. For minimizing the formation of N-[α-methyl-β-(β-methyl-β-hydroxycarbonyl)ethylthiopropionyl]-L-proline (7) from the above-mentioned precursors, it is recommendable to employ a pH not less than about 13, preferably a pH not less than about 13.5, more preferably not less than about 14.

As mentioned above, the reaction pH and the method of addition are important factors in preventing, among others, the formation of N-[α-methyl-β-(β-methyl-β-hydroxycarbonyl)ethylthiopropionyl]-L-proline (7) from the above-mentioned precursors during the deacylation reaction in the practice of the present invention.

As a typical deacylation reaction method, there may be mentioned, for example, the one which comprises using the reaction mixture containing, in the above-mentioned alkaline aqueous medium, the N-(D-α-methyl-β-acylthiopropionyl)-L-proline (3) together with the above-mentioned compounds of general formula (5) or formula (6), which are precursors of N-[α-methyl-β-(β-methyl-β-hydroxycarbonyl)-ethylthiopropionyl]-L-proline (7), or the active-carbon-treated solution, or crystals obtained therefrom and maintaining the pH at about 13 or higher until completion of the reaction. In this case, said alkaline aqueous medium may contain a required amount of alkali added in advance, or a required amount of alkali may be added successively or portionwise with the progress of the reaction to thereby maintain the pH at a desired level. Generally, by reason of simplicity, the former is preferred.

In the practice of the present invention, the deacylation reaction can be carried out at 70° C. or below, preferably at 50° C. or below and, generally, said reaction is carried out at around room temperature or below. For removing the heat generated, it is also desirable to cool, in advance, the reaction solution and/or the alkaline aqueous medium to be used.

When the deacylation reaction is carried out in an inert atmosphere such as a nitrogen atmosphere, the formation of oxidated by-products such as the disulfide can be suppressed to a level at which no problem is encountered at all. Therefore, in particular, such restriction of the alkali concentration in the step of deacylation as described in Japanese Kokai Publication Hei-3-169856 is unnecessary.

In the above-mentioned deacylation reaction, the reactant concentrations are not particularly limited but, for increasing the deposition of captopril in the crystallization step, said reaction is preferably carried out at a high N-(D-α-methyl-β-acylthiopropionyl)-L-proline (3) concentration of about 20 to 100% (w/v) relative to the aqueous medium.

In accordance with the present invention, high quality N-(D-α-methyl-β-mercaptopropionyl)-L-proline (4)

(captopril) can be obtained in high yields by subjecting the N-(D-α-methyl-β-acylthiopropionyl)-L-proline (3) obtained in the above manner by the Schotten-Baumann reaction to deacylation reaction in an alkaline aqueous medium and then, after acidification, causing crystallization of N-(D-α-methyl-β-mercaptopropionyl)-L-proline (4) (captopril) from the reaction mixture in aqueous medium, as detailedly mentioned hereinabove.

In particular, as mentioned above, the Schotten-Baumann reaction mixture or active-carbon-treated solution containing an N-(D-α-methyl-β-acylthiopropionyl)-L-proline (3) as the N-(α-methyl-β-acylthiopropionyl)-L-proline as obtained in accordance with the present invention contains various coexisting impurities at lower levels as compared with the reaction mixture obtained by the Schotten-Baumann reaction carried out in the conventional manner and, therefore, said reaction mixture or treated solution can be subjected as such to deacylation reaction without isolation of the N-(D-α-methyl-β-acylthiopropionyl)-L-proline (3), and the subsequent acidification can result in crystallization of high quality captopril in aqueous medium, in particular in aqueous solution. In particular, in case of the active-carbon-treated solution, not only the precursors of N-[α-methyl-β-(β-methyl-β-hydroxycarbonyl)ethylthiopropionyl]-L-proline (7) but also the unreacted D-α-methyl-β-acylthiopropionic acid halide (1) and the hydrolysis by-product D-α-methyl-β-acylthiopropionic acid, among others, which have an inhibitory effect on the crystallization of captopril in aqueous medium are removed and, therefore, the crystllization of captopril in aqueous medium is very easy and high quality captopril can be obtained. Thus, it is possible to realize a continuous process in aqueous medium, such as a process Schotten-Baumann reaction→deacylation reaction→captopril crystallization, or Schotten-Baumann reaction→active-carbon treatment→deacylation reaction→captopril crystallization, which process does not require the isolation of N-(D-α-methyl-β-acylthiopropionyl)-L-proline (3), namely a production process in which high quality captopril can be obtained by isolation in a simple and easy and efficient manner. It is no more necessary to extract and purify captopril using an organic solvent as described in Japanese Kokai Publication Hei-4-305565, Hei-5-17435, Hei-5-221966, etc.

In the practice of the present invention, for increasing the deposition of captopril in the step of captopril crystallization, the salting-out effect may be utilized as necessary; for example, an inorganic salt such as sodium chloride, potassium sulfate or lithium sulfate may be added or caused to be formed in the system, as described in Japanese Kokai Publication Sho-55-32063 and Hei-3-169856, for instance, or the captopril concentration and salt concentration may be increased by concentrating the system to a certain extent. On the other hand, a method may be applied to the present invention, in which the crystallization is caused by acidifying the system to a pH of 3 or below, preferably about 2 or below, at about 20° C. to 45° C. by gradually adding a mineral acid, such as hydrochloric acid, for example concentrated hydrochloric acid, or sulfuric acid, for example sulfuric acid with a concentration of at least about 50% or concentrated sulfuric acid so as to prevent captopril from becoming oily, and, finally, the system is cooled to about 0° C. to 5° C. to thereby increase the deposition. The thus-deposited captopril crystals are collected by filtration or centrifugation and generally dried under vacuum.

As detailedly described hereinabove, by employing the steps of:

① carrying out the Schotten-Baumann reaction under specified conditions;

② treating the Schotten-Baumann reaction mixture or crystals of the compound of general formula (3) with active carbon in the vicinity of neutral;

③ subjecting the Schotten-Baumann reaction mixture, either as such or after active-carbon treatment in the vicinity of neutral, to crystallization under specified conditions, and then collecting and/or storing the crystals; and ④ carrying out the deacylation under specific conditions in an aqueous medium containing at least one alkali selected from the group consisting of sodium hydroxide, potassium hydroxide and lithium hydroxide, either singly or in combination, captopril superior in quality, for example in terms of melting point, content and impurity content, to those captopril bulk substances so far reported can be produced from L-proline (2) and D-α-methyl-β-acetylthiopropionyl chloride in high yields not less than 75 mole percent and at low cost.

BEST MODES FOR CARRYING OUT THE INVENTION

The following examples are intended to describe the present invention in further detail and should by no means be construed as defining the scope of the invention.

In the following examples and reference examples, D-α-methyl-β-acetylthiopropionyl chloride was used as said D-α-methyl-β-acylthiopropionic acid halide (1) and N-(D-α-methyl-β-acetylthiopropionyl)-L-proline was used as said N-(α-methyl-β-acylthiopropionyl)-L-proline (3).

Furthermore, in the following examples and reference examples, all the procedures other than filtration, rinsing of crystals and downstream procedures were carried out under nitrogen atmosphere.

Moreover, in the examples and reference examples, the compound of general formula (5) and the compound of formula (6) are referred to briefly as compound (5) and compound (6), respectively. It should also be understood that in the examples and reference examples, the acyl group of compound (5) is acetyl.

EXAMPLES 1, 2, AND 3 AND REFERENCE EXAMPLE 1

To 101 g of deionized water was added 19.0 g (0.165 mol) of L-proline, and after cooling to about 5° C. and under agitation, a 30 wt. % aqueous solution of NaOH was added dropwise slowly to adjust the mixture to pH 9.5 to 9.9 at about 0° C. to 3° C. Under nitrogen gas and with the above-mentioned pH maintained, 29.2 9 (0.162 mol) of D-α-methyl-β-acetylthiopropionyl chloride was added dropwise over 1 hour at 0° C. to 3° C. with stirring at the agitation intensity indicated in Table 1. After completion of dropwise addition, the reaction was further continued until the consumption of a 30 wt. % aqueous solution of NaOH had ceased almost completely. The yields of various products in this reaction mixture are shown in Table 1. In Table 1, product 1 means N-acetyl-L-proline, product 2 means captopril, product 3 means compound (6), product 4 means compound (5)(n=2), and product means N-(D-α-methyl-β-acetylthiopropionyl)-L-proline. As shown in Table 1, the yield of product 5 is the molar yield based on D-α-methyl-β-acetylthiopropionyl chloride, the yields of products 1, 2, and 4 are weight percents relative to product 5, and the yield of product 3 is the area % relative to product 5.

TABLE 1

| | Agitation intensity | Product | | | | |
|---|---|---|---|---|---|---|
| | (kW/m³) | 1 | 2 | 3 | 4 | 5 |
| Reference Example 1 | <0.05 | 13% | 3.3% | 0.5 | 6% | 70% |
| Example 1 | ca. 0.1 | 5% | 0.4% | Not Detected | 3% | 90% |
| Example 2 | 0.2 to 0.4 | 2% | 0.2% | Not Detected | 2% | 95% |
| Example 3 | 1.3 to 1.5 | 1% | 0.2% | Not Detected | 1% | 97% |

EXAMPLE 4, 5, 6, 7, AND 8 AND REFERENCE EXAMPLE 2

To 101 g of deionized water was added 19.0 g (0.165 mol) of L-proline, and after cooling to about 5° C. and under agitation, a 30 wt. % aqueous solution of NaOH was added dropwise slowly at about 0° C. to 3° C. to adjust the mixture to the pH indicated in Table 2. Under nitrogen and with the above-mentioned pH maintained, 29.21 g (0.162 mol) of D-α-methyl-β-acetylthiopropionyl chloride was added dropwise over 1 hour at 0° C. to 3° C. with stirring at the agitation intensity of about 1 kW/m³. After completion of dropwise addition, the reaction was further continued until the consumption of a 30 wt. % aqueous solution of NaOH had ceased almost completely. The yields of various products in this reaction mixture are shown in Table 2. In Table 2, each of products 1 to 5 means the same as in Table 1. The yields of products 1 to 5 in Table 2 are as defined in Table 1. The yield ratio of compound (5)(n=3 and 4) to product 4 [namely, compound (5)(n=2)] was not more than 2 area % in Examples 4, 5, 6, 7, and 8 and not more than 6 area % in Reference Example 2.

TABLE 2

| | pH | Product | | | | |
|---|---|---|---|---|---|---|
| | | 1 | 2 | 3 | 4 | 5 |
| Example 4 | 7.4 to 7.9 | 0.4% | 0.2% | Not Dectected | 0.5% | 89% |
| Example 5 | 8.1 to 8.6 | 0.6% | 0.2% | Not Detected | 0.7% | 91% |
| Example 6 | 8.8 to 9.3 | 0.7% | 0.2% | Not Detected | 0.7% | 96% |
| Example 7 | 9.0 to 9.6 | 1.0% | 0.2% | Not Detected | 0.9% | 99% |
| Example 8 | 9.8 to 10.2 | 1.7% | 0.3% | Not Detected | 1.5% | 97% |
| Reference Example 2 | 10.3 to 10.6 | 4.8% | 0.6% | 0.2% | 4.1% | 92% |

EXAMPLE 9 AND REFERENCE EXAMPLES 3, 4, 5, AND 6

The Schotten-Baumann reaction mixture obtained in the same manner as Example 7 was adjusted to pH 7 by adding a 35 wt. % aqueous solution of HCl slowly under agitation at about 3° C. To 9.75 g of this aqueous solution [which contained 2.0 g of N-(D-α-methyl-β-acetylthiopropionyl)-L-proline together with 1.2 wt. % of compound (5)(n=2) based on N-(D-α-methyl-β-acetylthiopropionyl)-L-proline] was added 0.6 g of the additive shown in Table 3 and the mixture was stirred at room temperature for about 30 minutes. The additive was then filtered off and washed with about 6 ml of deionized water. The filtrate thus obtained was analyzed for the proportion of compound (5)(n=2) relative to N-(D-α-methyl-β-acetylthiopropionyl)-L-proline. The results are presented in Table 3. Incidentally, the recovery rate of N-(D-α-methyl-β-acetylthiopropionyl)-L-proline was invariably close to 100 wt. %.

TABLE 3

| | Additive | Compound (5) (n = 2) content |
|---|---|---|
| Example 9 | Active carbon | 0.3 wt. % |
| Reference Example 3 | Active clay | 1.2 wt. % |
| Reference Example 4 | Celite | 1.2 wt. % |
| Reference Example 5 | Alumina | 1.2 wt. % |
| Reference Example 6 | Silica gel | 1.2 wt. % |

EXAMPLE 10

Following the Schotten-Baumann reaction between D-α-methyl-β-acetylthiopropionyl chloride and L-proline in aqueous medium, 2.0 g of the harvested crystals of N-(D-α-methyl-β-acetylthiopropionyl)-L-proline [which contained 2.0 wt. % of compound (5)(n=2) based on N-(D-α-methyl-β-acetylthiopropionyl)-L-proline] were added to 25 ml of deionized water and the mixture was adjusted to pH 7 and dissolved by adding a 30 wt. % aqueous solution of NaOH slowly under agitation. To the resulting aqueous solution was added 0.7 g of active carbon and the mixture was stirred at room temperature for about 30 minutes. The carbon was then filtered off and washed with about 6 ml of deionized water. The filtrate thus obtained was analyzed. The recovery rate of N-(D-α-methyl-β-acetylthiopropionyl)-L-proline was approximately 99 wt. % and the proportion of compound (5)(n=2) relative to N-(D-α-methyl-β-acetylthiopropionyl)-L-proline was 0.5 wt. %.

REFERENCE EXAMPLE 7, 8, AND 9

The crystals of N-(D-α-methyl-β-acetylthiopropionyl)-L-proline as used in Example 10 [which contained compound (5) (n=2) in a proportion of 2.0 wt. % relative to N-(D-α-methyl-β-acetylthiopropionyl)-L-proline], 2.0 grams, were dissolved in 25 ml of the solvent shown in Table 4. To this solution was added 0.7 g of active carbon and the mixture was stirred at room temperature for about 30 minutes. The carbon was then filtered off and the filtrate was analyzed. The proportion of compound (5)(n=2) relative to N-(D-α-methyl-β-acetylthiopropionyl)-L-proline after active carbon treatment is shown in Table 4.

TABLE 4

| | Solvent | Compound (5) (n = 2) content |
|---|---|---|
| Reference Example 7 | Toluene | 2.3 wt. % |
| Reference Example 8 | Methanol | 1.9 wt. % |
| Reference Example 9 | Etanol | 1.7 wt. % |

EXAMPLES 11, 12, AND 13 AND REFERENCE EXAMPLE 10

The Schotten-Baumann reaction mixture obtained in the same manner as Example 6 was adjusted to pH 7 by adding a 35 wt. % aqueous solution of HCl slowly under agitation at about 3° C. To 19.75 g of this aqueous solution [which contained 4.1 g of N-(D-α-methyl-β-acetylthiopropionyl)-L-proline together with 0.8 wt. % of compound (5)(n=2)

based on N-(D-α-methyl-β-acetylthiopropionyl)-L-proline] was added active carbon in the amount indicated in Table 5 and the mixture was stirred at room temperature for about 30 minutes. The active carbon was then filtered off and washed with about 6 ml of deionized water. Under nitrogen, to the filtrate obtained was added 4N-NaOH/water [about 3.2 equivalents based on N-(D-α-methyl-β-acetylthiopropionyl)-L-proline] en bloc with stirring to make the pH not less than 13.1. This mixture was stirred at room temperature for about 15 minutes and after the deacetylation reaction had been completed under the same conditions, the reaction mixture was analyzed to find the proportion of N-[α-methyl-β-(β-methyl-β-hydroxycarbonyl)-ethylthiopropionyl]-L-proline (hereinafter referred to briefly as BA-CP) relative to captopril. The results are shown in Table 5.

TABLE 5

| | Amount of active carbon | BA-CP content |
|---|---|---|
| Reference Example 10 | — | 0.31 wt. % |
| Example 11 | 0.41 g | 0.13 wt. % |
| Example 12 | 0.82 g | 0.07 wt. % |
| Example 13 | 1.64 g | Not detected |

EXAMPLES 14, 15, AND 16

The Schotten-Baumann reaction mixture obtained in the same manner as Example 7 was adjusted to pH 7 by adding a 35 wt. % aqueous solution of HCl slowly at about 3° C. with stirring. This aqueous mixture, 50.0 g [which contained 10.3 g of N-(D-α-methyl-β-acetylthiopropionyl)-L-proline together with 1.3 wt. % of compound (5)(n=2) based on N-(D-α-methyl-β-acetylthiopropionyl)-L-proline and 1.2 wt. % of N-acetyl-L-proline based on N-(D-α-methyl-β-acetylthiopropionyl)-L-proline] was heated and stirred. At the temperature indicated in Table 6, the mixture was acidified with a 35 wt. % aqueous solution of HCl to let crystals deposit. In Examples 14 and 15, the 35 wt. % aqueous solution of HCl was added fast till pH 5 and, then, dropwise so that the pH dropped by about 0.2 in every 15 minutes till pH 3 to let crystals separate out gradually. Furthermore, the addition speed was gradually increased until the final pH 1.5 was established. In Example 16, the 35 wt. % aqueous solution of HCl was added fast till pH 5 and seed crystals were added at pH 4.7. Then, the HCl solution was added dropwise slowly so that the pH would drop by about 0.1 in every 15 minutes till pH 3 to let crystals separate out gradually. Then, the addition speed was gradually increased until the final pH 1.5 was established. The acidified mixture was allowed to cool gradually to room temperature and the gentle agitation was continued at room temperature for about 1 hour. The crystals that had separated out were harvested by filtration, rinsed with 23 ml of cold water, sufficiently drained, and dried in vacuo at about 40° C. The crystallization yield of the crystal obtained, N-(D-α-methyl-β-acetylthiopropionyl)-L-proline, and the proportions of compound (5)(n=2) and N-acetyl-L-proline are shown in Table 6.

TABLE 6

| | Acidification temperature | Crystallization yield | Compound (5) (n = 2) content | N-acetyl-L-proline content |
|---|---|---|---|---|
| Example 14 | 58 to 62° C. | 95% | 0.3 wt. % | 0.1 wt. % |
| Example 15 | 47 to 52° C. | 96% | 0.5 wt. % | 0.1 wt. % |
| Example 16 | 38 to 43° C. | 95% | 0.7 wt. % | 0.1 wt. % |

EXAMPLE 17

The same Schotten-Baumann reaction mixture as used in Examples 14, 15, and 16 (preadjusted to pH 7), 50.0 grams [which contained 10.3 g of N-(D-α-methyl-β-acetylthiopropionyl)-L-proline together with 1.3 wt. % of compound (5)(n=2) and 1.2 wt. % of N-acetyl-L-proline both based on N-(D-α-methyl-β-acetylthiopropionyl)-L-proline], was heated to about 70° C. and acidified to pH about 3 with a 35 wt. % aqueous solution of HCl under agitation to let an oil separate out. Then, this mixture was further acidified to pH 1.5. The mixture was cooled from 69° C. at the rate of about 0.5° C./15 min. to let crystals separate out gradually under intense agitation. After crystallization, the mixture was further cooled and maintained at about 40° C. for 30 minutes. The mixture was further cooled to room temperature with gentle stirring and, then, stirred gently at room temperature for about 1 hour. The crystals that had separated out were harvested by filtration, rinsed with 23 ml of cold water, drained well, and dried in vacuo at about 40° C. The crystallization yield of the crystal obtained, N-(D-α-methyl-β-acetylthiopropionyl)-L-proline, was 95% and the proportions of compound (5)(n=2) and N-acetyl-L-proline were 0.3 wt. % and 0.1 wt. %, respectively.

EXAMPLE 18

The same Schotten-Baumann reaction mixture as used in Examples 14, 15, and 16 (preadjusted to pH 7), 50.0 grams [which contained 10.3 g of N-(D-α-methyl-β-acetylthiopropionyl)-L-proline together with 1.3 wt. % of compound (5)(n=2) and 1.2 wt. % of N-acetyl-L- proline both based on N-(D-α-methyl-β-acetylthiopropionyl)-L-proline], was acidified to pH 1.5 by adding a 35 wt. % aqueous solution of HCl at 22° C. to 25° C. with stirring to let crystals separate out. The addition of the 35 wt. % aqueous solution of HCl was carried out in the manner described in Example 12. After the final pH 1.5 was established, gentle agitation was continued at room temperature for about 1 hour. When a small amount of this whip-like slurry was recovered by filtration and washed with cold water, the proportion of compound (5) (n=2) was found to be 12 wt. %. The above slurry was heated at about 75° C. to provide an oil. This oil was cooled in the manner described in Example 17 to harvest crystals. The crystallization yield of the crystal obtained, N-(D-α-methyl-β-acetylthiopropionyl)-L-proline, was 95% and the proportions of compound (5)(n=2) and N-acetyl-L-proline were 0.4 wt. % and 0.1 wt. %, respectively.

REFERENCE EXAMPLE 11

The same Schotten-Baumann reaction mixture as used in Examples 14, 15, and 16 (preadjusted to pH 7), 50.0 grams [which contained 10.3 g of N-(D-α-methyl-β-acetylthiopropionyl)-L-proline together with 1.3 wt. % of compound (5)(n=2) and 1.2 wt. % of N-acetyl-L-proline both based on N-(D-α-methyl-β-acetylthiopropionyl)-L- proline], was acidified to pH 1.5 by adding a 35 wt. % aqueous solution of HCl thereto at 22° C. to 25° C. with stirring to let crystals separate out and gentle stirring was continued for about 1 hour at room temperature. The resulting whip-like slurry was recovered by filtration, washed with 23 ml of cold water, drained well, and dried in vacuo at about 40° C. The crystallization yield of N-(D-α-methyl-β-acetylthiopropionyl)-L-proline was 96% and the proportions of compound (5)(n=2) and N-acetyl-L-proline were 12 wt. % and 0.2 wt. %, respectively.

REFERENCE EXAMPLE 12

The filtrability of the slurries, liquid contents of the wet crystals, and crystal properties in Examples 14, 15, 16, 17, and 18 and Reference Example 11 were compared. The results are presented in Table 7.

TABLE 7

| | Flow-through speed (m³/m²/h) | | | Liquid content of wet crystal (on a wet basis) | Description of crystals |
|---|---|---|---|---|---|
| | A | B | C | | |
| Example 14 | 8.8 | 8.8 | 11.8 | 17 wt. % | Glossy large rods |
| Example 15 | 7.3 | 8.8 | 10.6 | 23 wt. % | Glossy large rods |
| Example 16 | 6.2 | 5.9 | 8.2 | 28 wt. % | Glossy medium-size rods |
| Example 17 | 10.6 | 10.6 | 10.6 | 17 wt. % | Glossy large rods |
| Example 18 | 8.8 | 11.8 | 11.8 | 18 wt. % | Glossy large rods |
| Reference Example 11 | 3.9 | 2.8 | 4.2 | 37 wt. % | Small rods or needless |

The slurry obtained in Reference Example 11 could be withdrawn only in a very long time. Therefore, the comparison of filtrability was made in terms of the filtration speeds determined by the following three methods. The flow-through speeds were evaluated by the same suction filtration method using a 40 mm (dia.) filter paper.

A: The wet cake was adjusted to a uniform thickness and the filtrate was passed.

B: The wet cake was spread to drain sufficiently and the filtrate was passed.

C: The wet cake was spread to drain sufficiently and 23 ml of cold water was passed.

EXAMPLES 19 AND 20

The same crystals of N-(D-α-methyl-β-acetylthiopropionyl)-L-proline as used in Example 10 [which contained 2.0 wt. % of compound (5)(n=2)], 2.0 grams, were added to 20 ml of deionized water and the mixture was adjusted to the pH shown in Table 8 by adding a 30 wt. % aqueous solution of NaOH slowly under stirring. To the aqueous solution thus obtained was added 0.8 g of active carbon and the mixture was stirred at room temperature for about 10 minutes. The carbon was then filtered off and washed with about 8 ml of deionized water. The filtrate was treated in the same manner as described in Example 11 to let crystals separate out. The slurry thus obtained was washed with 10 ml of water, drained well, and-dried in vacuo at about 40° C. The proportion of compound (5)(n=2) in the crystal, N-(D-α-methyl-β-acetylthiopropionyl)-L-proline thus obtained is shown in Table 8.

TABLE 8

| | pH for active-carbon-treatment | Compound (5) (n = 2) content |
|---|---|---|
| Example 19 | 5.8 | <0.1 wt. % |
| Example 20 | 9.2 | <0.1 wt. % |

EXAMPLE 21

To 84 g of deionized water was added 19.0 g (0.165 mol) of L-proline and the mixture was cooled to about 5° C. Under agitation, a 30 wt. % aqueous solution of NaOH was added dropwise slowly at about 0° C. to 3° C. to adjust the pH to 7.3 to 7.9. Under nitrogen gas and with the above-mentioned pH maintained, 29.2 g (0.162 mol) of D-α-methyl-β-acetylthiopropionyl chloride was added dropwise over about 15 hours with stirring at 0° C. to 3° C. 0 After completion of dropwise addition, the reaction was further continued until the consumption of a 30 wt. % aqueous solution of NaOH had ceased almost completely. This reaction mixture was adjusted to pH 7 by adding a 35 wt. % aqueous solution of HCl slowly thereto at about 3° C. with constant stirring. To this aqueous solution was added 4.2 g of active carbon and the mixture was stirred at room temperature for about 30 minutes. The carbon was then filtered off and washed with about 36 ml of deionized water. The filtrate was heated under agitation and acidified to pH about 1.5 with a 35 wt. % aqueous solution of HCl at about 70° C. This solution was cooled at a rate of about 0.5° C. /15 min. to let crystals separate out slowly under intense agitation. After this crystallization, the reaction mixture was further cooled to room temperature under gentle agitation and this gentle agitation was continued at room temperature for about 1 hour. The crystals were harvested by filtration, rinsed with about 56 ml of cold water, drained well, and dried in vacuo at about 40° C. The yield of N-(D-α-methyl-β-acetylthiopropionyl)-L-proline was 35.2 g (0.135 mol) or 84 mol % based on D-α-methyl-β-acetylpropionyl chloride. The proportion of compound (5)(n=2) was 0.1 wt. %.

EXAMPLE 22

The same crystals of N-(D-α-methyl-β-acetylthiopropionyl)-L-proline as used in Example 10 [which contained 2.0 wt. % of compound (5)(n=2)], 100 grams, was added to a 30 wt. % aqueous solution of NaOH (about 3.2 equivalents of NaOH based on N-(D-α-methyl-β-acetylthiopropionyl)-L-proline) over about 25 minutes under agitation. After completion of addition, the reaction was continued for about 10 minutes. The reaction temperature was consistently controlled at 0° C. to 5° C. and the reaction pH was maintained over 13.2 throughout. Analysis by HPLC revealed that the reaction rate was 100% and that the proportion of N-(α-methyl-β-(β-methyl-β-hydroxycarbonyl)ethylthiopropionyl)-L-proline relative to captopril was 0.5 wt. %.

EXAMPLE 23

The same crystals of N-(D-α-methyl-β-acetylthiopropionyl)-L-proline as obtained in Example 14 [which contained 0.3 wt. % of compound (5)(n=2)], 14.0 grams, was added to a mixture of 34 ml of deionized water and 23.0 g of 30 wt. % NaOH/H₂O over 5 hours at a constant internal temperature of 30° C. under agitation. After completion of addition, the stirring was further continued at 30° C. for 1 hour. The final pH was 13.4. Analysis of the reaction mixture revealed that there was no residue of N-(D-α-methyl-β-acetylthiopropionyl)-L-proline and that the yield of captopril was 99 mol %. The proportion of BA-CP relative to captopril was less than 0.1 wt. %.

EXAMPLES 24 AND 25 AND REFERENCE EXAMPLE 13

The same crystals of N-(D-α-methyl-β-acetylthiopropionyl)-L-proline as prepared in Example 14 [which contained 0.3 wt. % of compound (5)(n=2)], 14.0 grams, was added to a mixture of 34 ml of deionized water and 30 wt. % NaOH/H$_2$O over 30 minutes at a constant internal temperature of about 5° C. under agitation. In the course following the start of addition of N-(D-α-methyl-β-acetylthiopropionyl)-L-proline crystals till completion of the reaction, a 30 wt. % aqueous solution of NaOH was added so as to maintain the pH at the level indicated in Table 9. After completion of the reaction, the reaction mixture was analyzed for the yield of captopril and the proportion of BA-CP relative to captopril. The results are shown in Table 9.

TABLE 9

|  | pH | Yield of captopril | BA-CP content |
| --- | --- | --- | --- |
| Reference Example 13 | 12.8 | 99 mol % | 0.2 wt. % |
| Example 24 | 13.6 | 99 mol % | <0.1 wt. % |
| Example 25 | 14.5 | 99 mol % | <0.1 wt. % |

EXAMPLE 26

The Schotten-Baumann reaction was carried out in the same manner as Example 4 except that 12 g of active carbon was fed at the point of time when about three-quarters of the necessary amount of D-α-methyl-β-acetylthiopropionyl chloride had been added. The proportion of by-products relative to N-(D-α-methyl-β-acetylthiopropionyl)-L-proline in the reaction mixture were as follows.

N-acetyl-L-proline: 1 to 2 wt. %
Captopril 0.2 wt. %
Compound (6) : not detected
Compound (5)(n=2) : not detected

EXAMPLE 27

To 203 g of deionized water were added 38.0 g (0.330 mol) of L-proline and 74.9 g (0.748 mol) of potassium hydrogencarbonate and the mixture was cooled to about −3° C. to 0° C. Under nitrogen and with constant agitation, 58.4 g (0.324 mol) of D-α-methyl-β-acetylthiopropionyl chloride was added dropwise over 4 hours at −3° C. to 0° C. After completion of dropwise addition, the reaction was further continued under the same conditions for 1 hour. The yield of N-(D-α-methyl-β-acetylthiopropionyl)-L-proline based on D-α-methyl-β-acetylthiopropionyl chloride in the reaction mixture was 89 mol % and the proportion of compound (5)(n=2) relative to N-(D-α-methyl-β-acetylthiopropionyl)-L-proline was 0.1 wt. % During the reaction, the range of pH was 7.4 to 8.8.

EXAMPLE 28

To 110 g of deionized water were added 19.0 g (0.165 mol) of L-proline and 33.0 g (0.330 mol) of potassium hydrogencarbonate and the mixture was cooled to about −3° C. to 0° C. Under nitrogen and with constant agitation, 29.2 g (0.162 mol) of D-α-methyl-β-acetylthiopropionyl chloride was added dropwise over 1 hour at −3° C. to 0° C. After completion of dropwise addition, the reaction was further continued under the same conditions for 1 hour. The yield of agitation, a 30 wt. % aqueous solution of NaOH was gradually added dropwise at about 0° C. to 3° C. so as to adjust the pH to 9.3. Under nitrogen and with the pH maintained at 9.4 to 9.7, 31.3 g (0.173 mol) of D-α-methyl-β-acetylthiopropionyl chloride was added dropwise over about 1 hour at 2° C. to 5° C. with stirring at an agitation intensity of about 1.5 kW/m$^3$. After completion of dropwise addition, the reaction was further continued under the same conditions for about 2 hours. Under nitrogen, this reaction mixture was adjusted to pH 7 with 35 wt. % HCl/H$_2$O at about 1° C. To this solution was added 15.0 g of active carbon and the mixture was stirred under nitrogen at about 20° C. for 1 hour. The carbon was then filtered off and washed with about 100 ml of deionized water. Under nitrogen gas, the filtrate was added to 3.4N-NaOH/H$_2$O [about 3.4 equivalents of NaOH based on N-(D-α-methyl-β-acetylthiopropionyl)-L-proline] over about 30 minutes at a constant internal temperature of about 2° C. to 7° C. with stirring. The reaction was further continued under nitrogen for about 2 hours. The final pH was over 13.0. Then, 35 wt. % HCl/H$_2$O was added dropwise so as to bring the pH to 7. At an internal temperature of about 20° C. sodium chloride was added till substantial saturation and the mixture was further stirred for about 1 hour. At an internal temperature of about 20° C. to 30° C. 35 wt. % HCl/H$_2$O was slowly added dropwise under intense stirring until the pH became 3.4 and this intense stirring was further continued for about 1 hour. To the resulting slurry was added a further amount of 35 wt. % HCl/H$_2$O dropwise over more than 1 hour at an internal temperature of about 20° C. to 30° C. to bring the pH to 3.0 and the intense stirring was continued for 1 hour. Then, at an internal temperature of about 20° C. to 30° C. 35 wt. % HCl/H$_2$O was added dropwise over about 1 hour to adjust the pH to 1. The intense stirring was further continued in this condition for 30 minutes and the mixture was cooled to an internal temperature of 2° C. At this internal temperature of about N-(D-α-methyl-β-acetylthiopropionyl)-L-proline based on D-α-methyl-β-acetylthiopropionyl chloride in the reaction mixture was 81 mol %. Compound (5)(n=2) was not detected. The range of pH was 7.2 to 8.9 during the reaction.

EXAMPLE 29

To 85 g of deionized water was added 19.0 g (0.165 mol) of L-proline and the mixture was cooled to about 5° C. Under agitation, a 30 wt. % aqueous solution of NaOH was slowly added dropwise at about 0° C. to 3° C. so as to adjust the pH to 8.5. Then, under nitrogen and with the pH maintained between 8.3 and 8.7, 29.2 g (0.162 mol) of D-α-methyl-β-acetylthiopropionyl chloride was added dropwise over about 1 hour at 2° C. to 5° C. with stirring at an agitation intensity of about 1.5 kW/m$^3$. After completion of dropwise addition, the reaction was further continued under the same conditions for about 2 hours. Under nitrogen, the reaction mixture thus obtained was adjusted to pH 4.5 to 5.0 by adding a 35 wt. % aqueous solution of HCl thereto dropwise at about 1° C. and, then, heated to about 60° C. Under intense agitation, 35 wt. % HCl/H$_2$O was further added so as to reduce the pH by about 0.2 in every 15 minutes until the pH reached 2.5 to let crystals separate out. After gradual cooling to about 10° C. a further amount of 35 wt. % HCl/H$_2$O was added so as to adjust the pH to 1.5 and the mixture was further stirred gently for about 1 hour. The crystals that had separated out were harvested by filtration, drained well, rinsed with about 60 ml of cold water, and drained well again to provide wet crystals of N-(D-α-methyl-β-acetylthiopropionyl)-L-proline [yield 89%; containing 0.2 wt. % of compound (5)(n=2) and not more than 0.1 wt. % of N-acetyl-L-proline].

EXAMPLE 30

To 101 g of deionized water was added 19.0 g (0.165 mol) of L-proline and the mixture was cooled to about 5° C. Under 2° C., the intense stirring was continued for 4 hours. The resulting slurry was separated and washed twice with about 15 ml of cold water. The wet crystals thus obtained were dried in vacuo (1 to 5 mmHg) at a temperature not over 40° C. The yield of captopril was 28.2 g (0.130 mol) or 79 mol % based on L-proline and 75 mol % based on D-α-methyl-β-acetylthiopropionyl chloride.

The description and properties of the product captopril were as follows.

White crystals, substantially odorless m.p. 106° C. (melting-point standard: acetanilide)

$[\alpha]_D^{25}$ =−128° C. (c=1.0, EtOH, 100 mm)

HPLC purity 99.5 wt. %

Titrimetric purity 99.5%

Disulfide content 0.2 wt. %

β-Mercapto-α-methylpropionic acid content <0.1 wt. %

N-[α-methyl-β-(β-methyl-β-hydroxycarbonyl)-ethylthiopropionyl]-L-proline content <0.1 wt. %

N-acetyl-L-proline content 0.1 wt. %

Otherwise, no specific impurity was detected on the HPLC.

EXAMPLE 31

To 85 g of deionized water was added 19.0 g (0.165 mol) of L-proline and the mixture was cooled to about 5° C. Under agitation, a 30 wt. % aqueous solution of NaOH was slowly added dropwise at 0° C. to 3° C. to bring the pH to 9.0. Under nitrogen and with the pH maintained at 8.9 to 9.4, 29.2 g (0.162 mol) of D-α-methyl-β-acetylthiopropionyl chloride was added dropwise over about 1 hour at 2° C. to 5° C. with stirring at an agitation intensity of about 1.5 kW/m³. After completion of dropwise addition, the reaction was further continued under the same conditions for about 2 hours. Under nitrogen, this reaction mixture was adjusted to pH 7 by adding 35 wt. % HCl/H₂O dropwise thereto at about 1° C. and, then, heated to about 60° C. Then, under intense stirring, the mixture was acidified with 35 wt. % HCl/H₂O to let crystals separate out in a nitrogen atmosphere. The 35 wt. % aqueous solution of HCl was added fast till pH 5 and, then, dropwise at a rate of pH about 0.2/15 min. till pH 3 to let crystals separate out slowly. The addition speed was then increased gradually until the final pH 1.5 was established. Then, the reaction mixture was gradually cooled to about 10° C. and stirred gently for about 2 hours. The crystals were harvested by filtration, drained well, rinsed with about 60 ml of cold water, and drained well to provide wet crystals of N-(D-α-methyl-β-acetylthiopropionyl)-L-proline (yield 89%, compound (5)(n=2) content 0.2 wt. %). Under nitrogen, the wet crystals were added to 3.4N-NaOH/H₂O (about 3.3 equivalents of NaOH based on N-(D-α-methyl-β-acetylthiopropionyl)-L-proline) over about 30 minutes at a constant internal temperature of about 2° C. to 7° C. with agitation. The reaction was further continued under nitrogen for about 2 hours and at the stage of pH about 14, 35 wt. % HCl/H₂O was added dropwise so as to adjust the reaction mixture to pH 7. Then, at an internal temperature of about 3° C. to 25° C., sodium chloride was added until substantial saturation and the mixture was stirred for about 1 hour. At an internal temperature of 40° C. 35 wt. % HCl/H₂O was slowly added dropwise to bring the pH to 3.4 under intense agitation and the intense agitation was continued for about 1 hour. To the resulting slurry, at an internal temperature of 40° C. was added a further amount of 35 wt. % HCl/H₂O dropwise over about 1 hour to lower the pH to 3.0 and the mixture was stirred intensely for 1 hour. Then, at an internal temperature of 40° C. a further amount of 35 wt. % HCl/H₂O was added dropwise over 20 minutes to bring the pH to 1.8. The intense stirring was continued for 30 minutes and with the pH maintained at 1.8 by dropwise addition of 35 wt. % HCl/H₂O, the mixture was cooled to an internal temperature of 4° C. The reaction mixture was further cooled to about 1° C. and maintained under intense agitation at that temperature for 30 minutes. The resulting slurry was filtered and washed twice with about 15 ml portions of cold water. The wet crystals thus obtained were dried in vacuo (1 to 5 mmHg) at a temperature not exceeding 40° C. The yield of captopril was 27.5 g (0.127 mol). The yield of captopril based on L-proline was 77 mol % and that based on D-α-methyl-β-acetylthiopropionyl chloride was 78 mol %.

The description and properties of the above product captopril were as follows.

White crystals, substantially odorless m.p. 107° C. to 108° C. (melting-point standard: acetanilide)

$[\alpha]_D^{25}$=−128° C. (c=1.0 EtOH, 100 mm)

HPLC purity 99.7 wt. %

Titrimetric purity 99.7%

Disulfide content 0.1 wt. %

β-Mercapto-α-methylpropionic acid content <0.1%

N-[α-methyl-β-(β-methyl-β-hydroxycarbonyl)-ethylthiopropionyl]-L-proline content <0.1 wt. %

N-acetyl-L-proline content 0.1 wt. %

No other impurity peak was detected on the HPLC.

EXAMPLE 32

To 85 g of deionized water was added 19.0 g (0.165 mol) of L-proline and the mixture was cooled to about 5° C. Under agitation, a 30 wt. % aqueous solution of NaOH was slowly added dropwise thereto at about 0° C. to 3° C. to bring the pH to 9.5. Under nitrogen and with the pH maintained at 9.3 to 9.7, 29.2 g (0.162 mol) of D-α-methyl-β-acetylthiopropionyl chloride was added dropwise over about 1 hour at 2° C. to 5° C. with stirring at an agitation intensity of about 1.5 kW/m³. After completion of dropwise addition, the ripening reaction was continued under the same conditions for about 1 hour. This reaction mixture was adjusted to pH 7 by dropwise addition of 35 wt. % HCl/H₂O at about 1° C. under nitrogen gas.

To this solution was added 12.0 g of active carbon and the mixture was stirred at about 20° C. under nitrogen for 2 hours.

The carbon was then filtered off and washed with 55 ml of deionized water. This solution was adjusted to pH 7 and heated to about 50° C. under nitrogen gas. Under intense agitation, the mixture was acidified with 35 wt. % HCl/H₂O to let crystals separate out under nitrogen gas. The 35 wt. % aqueous solution of HCl was added fast till pH 5 and dropwise at a rate of pH about 0.2/15 min. till pH 3 to let crystals separate out slowly. The addition speed was then increased to adjust the pH to 1.5. The reaction mixture was gradually cooled to about 10° C. and stirred gently for about 2 hours. The crystals that had separated out were harvested by filtration, drained well, rinsed with about 60 ml of cold water, and drained well to provide wet crystals of N-(D-α-methyl-β-acetylthiopropionyl)-L-proline (yield~90%; compound (5)(n=2) content <0.1 wt. %). The wet crystals thus obtained were added to 3.4N-NaOH/H₂O (about 3.2 equivalents of NaOH based on N-(D-α-methyl-β-acetylthiopropionyl)-L-proline) over 30 minutes in a nitrogen gas at an internal temperature of about 2° C. to 7° C. under constant agitation. The reaction was further continued under nitrogen gas for about 2 hours and at the stage of pH 13.5, the reaction mixture was adjusted to pH 7 by dropwise addition of 35 wt. % HCl/H₂O. Then, at an internal temperature of about 3° C. to 25° C. about 30 g of sodium chloride was added and the mixture was stirred for about 1 hour. At an internal temperature of 30° C., 35 wt. % HCl/H₂O was slowly added dropwise to bring the pH to 3.4 under intense agitation and the intense stirring was continued for about 1 hour. To the resulting slurry, at an internal temperature of 30° C., was added a further amount of 35 wt. % HCl/H₂O dropwise over not less than 1 hour to lower the pH to 3.0. The intense stirring was then continued for 1 hour. Then, at an internal temperature of 30° C., 35 wt. % HCl/H₂O was added dropwise over 20 minutes to bring the pH to 1.8. The mixture was further stirred for 30 minutes and with the pH maintained with 35 wt. % HCl/H₂O, the reaction mixture was cooled to an internal temperature of 4° C. The temperature was further lowered to about 1° C. and the mixture was stirred gently for 30 minutes. The resulting slurry was filtered and washed twice with about 15 ml portions of cold water. The wet crystals were then dried in vacuo (1 to 5 mmHg) at about 40° C. The yield of captopril was 27.3 g (0.126 mol). The yield based on L-proline was 76 mol % and the yield based on D-α-methyl-β-acetylthiopropionyl chloride was 78 mol %.

The description and properties of the product captopril were as follows.

White crystals, substantially odorless m.p. 107° C. to 108° C. (melting-point standard: acetanilide) $[\alpha]_D^{25}=-129°$ C. (c=1.0, EtOH, 100 mm)

HPLC purity 99.9 wt. %

Titrimetric purity 99.9%

Disulfide content 0.1 wt. %

ββ-Mercapto-α-methylpropionic acid content <0.1%

N-[α-methyl-β-(β-methyl-β-hydroxycarbonyl)-ethylthiopropionyl]-L-proline content <0.1 wt. %

N-acetyl-L-proline content <0.1 wt. %

Otherwise, no specific impurity peak was detected on the HPLC.

REFERENCE EXAMPLE 14

Using the various reaction mixtures [the proportion of N-(α-methyl-β-(β-methyl-β-hydroxycarbonyl) ethylthiopropionyl)-L-proline relative to captopril: 0.1 to 3.0 wt. %] obtained by the deacylation reaction, which was carried out in the same manner as described in the foregoing examples and reference examples, of several grades of N-(D-α-methyl-β-acetylthiopropionyl)-L-proline varying in compound (5) and compound (6) contents, captopril was crystallized out in the same manner as described in Examples 27 to 29 and the harvested crystals were rinsed and dried to provide captopril crystals (yields: about 85 mol %). The elimination rate of N-(α-methyl-β-(α-methyl-β-hydroxycarbonyl)ethylthiopropionyl)-L-proline in the product captopril was not higher than about 50% and the elimination rate tended to be fairly low when the N-(α-methyl-β-β-methyl-β-hydroxycarbonyl)ethylthiopropionyl)-L-proline content was low. It was, therefore, found very difficult to remove N-(α-methyl-β-(β-methyl-β-hydroxycarbonyl)-ethylthiopropionyl)-L-proline from captopril with efficiency while upholding the yield of water-soluble captopril.

INDUSTRIAL APPLICABILITY

In accordance with the present invention, there is provided a highly expedient and efficient process for producing a high-melting, high-quality grade of N-(D-α-methyl-β-mercaptopropionyl)-L-proline (4) (captopril) with minimal impurities, particularly with a very low content of N-[α-methyl-β-(β-methyl-β-hydroxycarbonyl)-ethylthiopropionyl)-L-proline (7) and other impurities difficult to remove, in high yields and at low cost. There can also be provided a highly expedient and efficient process for producing a high quality N-(D-α-methyl-β-acylthiopropionyl)-L-proline (3) or N-(DL-α-methyl-β-acylthiopropionyl)-L-proline, which is an intermediate for the synthesis of N-(D-α-methyl-β-mercaptopropionyl)-L-proline (4) (captopril), with a minimal content of precursors of N-[α-methyl-β-(β-methyl-β-hydroxycarbonyl) ethylthiopropionyl]-L-proline (7) and other impurities, in high yields and at low cost.

We claim:

1. A process for producing high purity N-(D-α-methyl-β-mercaptopropionyl)-L-proline of the formula (4)

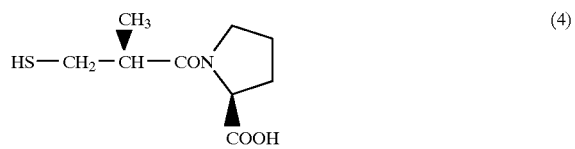

by subjecting a D-α-methyl-β-acylthiopropionic acid halide of the general formula (1)

(wherein R¹ represents an acyl group and X represents a halogen), and L-proline of the formula (2)

to Schotten-Baumann reaction in a basic aqueous medium in the presence of a deacidifying condensing agent to give the corresponding N-(D-α-methyl-β-acylthiopropionyl)-L-proline of the general formula (3)

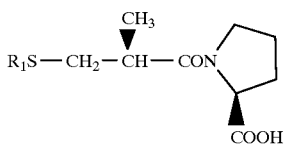

(wherein $R^1$ is as defined above), followed by deacylation, which comprises carrying out the deacylation of the N-(D-α-methyl-β-acylthiopropionyl)-L-proline after removal of those impurities concurrently formed with the above-mentioned objective substance N-(D-α-methyl-β-mercaptopropionyl)-L-proline, in their precursor stage, from the aqueous medium solution after commencement but before completion of said Schotten-Baumann reaction or after completion thereof by treating said aqueous medium solution with active carbon at a pH not higher than 12 wherein the aqueous medium is water essentially free of any organic solvent.

2. The process according to claim 1, wherein, in the Schotten-Baumann reaction, said D-α-methyl-β-acylthiopropionic acid halide (1) is used in the form of DL-α-methyl-β-acylthiopropionic acid halide to give the N-(DL-α-methyl-β-acylthiopropionyl)-L-proline, which is then subjected to optical resolution to give the N-(D-α-methyl-β-acylthioproplonyl)-L-proline (3).

3. The process according to claim 1, wherein the Schotten-Baumann reaction is carried out at a temperature of 10° C. or below and a pH of 7.3 to 10.2 with stirring at an intensity of 0.1 kW/m³ or more.

4. The process according to claim 1, wherein the deacylation is carried out at a pH not less than 13 in an aqueous medium containing at least one alkali selected from the group consisting of sodium hydroxide, potassium hydroxide and lithium hydroxide.

5. The process according to claim 1, wherein the acyl group is acetyl.

6. A process for producing high purity N-(D-α-methyl-β-mercaptopropionyl)-L-proline of the formula (4)

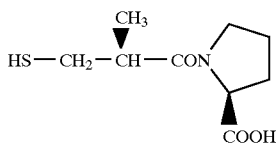

by subjecting a D-α-methyl-β-acylthiopropionic acid halide of the general formula (1)

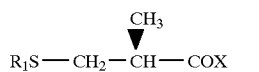

(wherein $R^1$ represents an acyl group and X represents a halogen), and L-proline of the formula (2)

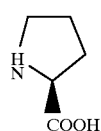

to Schotten-Baumann reaction in a basic aqueous medium in the presence of a deacidifying condensing agent to give the corresponding N-(D-α-methyl-β-acylthiopropionyl)-L-proline of the general formula (3)

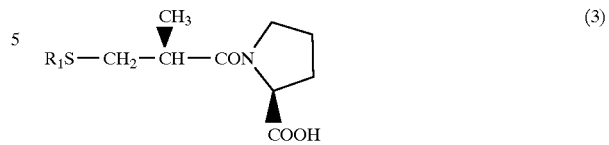

(wherein $R^1$ is as defined above), followed by deacylation, which comprises collecting the N-(D-α-methyl-β-acylthiopropionyl)-L-proline by causing the same to perform crystallization at 35° C. to 100° C. under acidic conditions from the aqueous medium solution after completion of the Schotten-Baumann reaction, thus removing those impurities concurrently formed with the above-mentioned objective substance N-(D-α-methyl-β-mercaptopropionyl)-L-proline, in their precursor stage, and subjecting the thus-collected N-(D-α-methyl-β-acylthiopropionyl)-L-proline, either as such or after storage, to the deacylation wherein the aqueous medium is water essentially free of any organic solvent.

7. The process according to claim 6, wherein the crystallization of the N-(D-α-methyl-β-acylthiopropionyl)-L-proline (3) is carried out after active-carbon-treatment of the aqueous medium solution after commencement but before completion of the Schotten-Baumann reaction or after completion thereof.

8. The process according to claim 6, wherein, in the Schotten-Baumann reaction, the D-α-methyl-β-acylthiopropionic acid halide (1) is used in the form of DL-α-methyl-β-acylthiopropionic acid halide to give the N-(DL-α-methyl-β-acylthiopropionyl)-L-proline, followed by optical resolution to give the N-(D-α-methyl-β-acylthiopropionyl)-L-proline (3).

9. The process according to claim 6, wherein the crystallization is carried out at 40° C. to 70° C.

10. The process according to claim 6, wherein the Schotten-Baumann reaction is carried out at a temperature of 10° C. or below and a pH of 7.3 to 10.2 with stirring at an intensity of 0.1 kW/m³ or more.

11. The process according to claim 6, wherein the deacylation is carried out at a pH not less than 13 in an aqueous medium containing at least one alkali selected from the group consisting of sodium hydroxide, potassium hydroxide and lithium hydroxide.

12. The process according to claim 6, wherein the acyl group is acetyl.

13. A process for producing a high purity N-(D-α-methyl-β-acylthiopropionyl)-L-proline which comprises treating with active carbon at a pH of 12 or below an aqueous medium solution of the N-(D-α-methyl-β-acylthiopropionyl)-L-proline of the general formula (3)

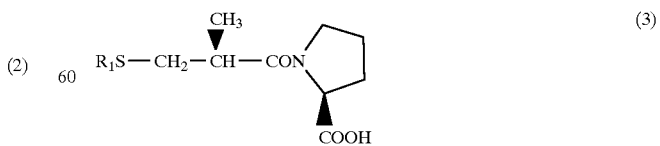

(wherein $R^1$ is an acyl group), which solution contains at least one impurity selected from the group consisting of compounds of the general formula (5)

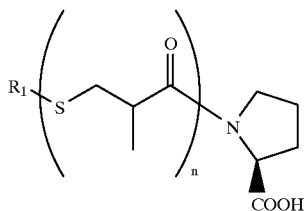

(5)

(wherein n is an integer of 2 to 4 and $R^1$ is as defined above), and the compound of the formula (6)

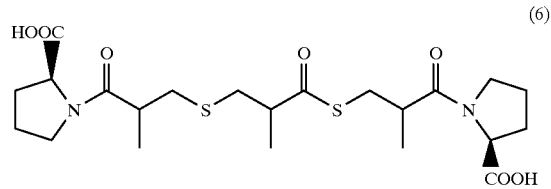

(6)

to thereby remove the compound or compounds, coexisting as impurities, of the general formula (5) and the formula (6) wherein the aqueous medium is water essentially free of any organic solvent.

14. The process according to claim 13, wherein said N-(D-α-methyl-β-acylthiopropionyl)-L-proline (3) is used in the form of N-(DL-α-methyl-β-acylthiopropionyl)-L-proline.

15. The process according to claim 13, wherein the acyl group is acetyl.

16. A process for producing a high purity N-(D-α-methyl-β-acylthiopropionyl)-L-proline which comprises causing an N-(D-α-methyl-β-acylthiopropionyl)-L-proline of the general formula (3)

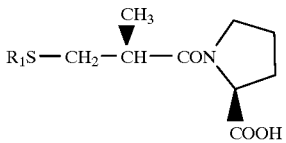

(3)

(wherein $R^1$ is an acyl group), to perform crystallization at 35° C. to 100° C. under acidic conditions from an aqueous medium solution of the compound of general formula (3) containing at least one impurity selected from the group consisting of compounds of the general formula (5)

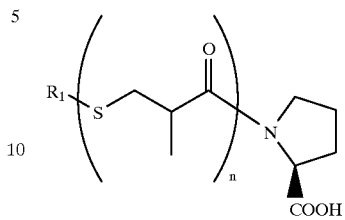

(5)

(wherein n is an integer of 2 to 4 and $R^1$ is as defined above), and the compound of the formula (6)

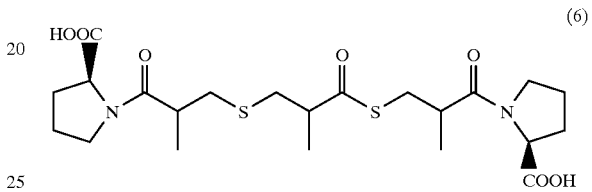

(6)

to thereby remove the compound or compounds, coexisting as impurities, of the general formula (5) and the formula (6) wherein the aqueous medium is water essentially free of any organic solvent.

17. The process according to claim 16, wherein said N-(D-α-methyl-β-acylthiopropionyl)-L-proline (3) is used in the form of N-(DL-α-methyl-β-acylthiopropionyl)-L-proline.

18. The process according to claim 16 wherein the crystallization is carried out at 40° C. to 70° C.

19. The process according to claim 16, wherein the acyl group is acetyl.

* * * * *